(12) United States Patent
Krag et al.

(10) Patent No.: US 7,098,302 B2
(45) Date of Patent: Aug. 29, 2006

(54) BINDING PEPTIDES SPECIFIC FOR THE EXTRACELLULAR DOMAIN OF ERBB2 AND USES THEREFOR

(75) Inventors: David N. Krag, Shelburne, VT (US); Stephanie C. Pero, Burlington, VT (US); Lyn Oligino, South Burlington, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 593 days.

(21) Appl. No.: 10/272,437

(22) Filed: Oct. 15, 2002
(Under 37 CFR 1.47)

(65) Prior Publication Data

US 2003/0216309 A1    Nov. 20, 2003

Related U.S. Application Data

(60) Provisional application No. 60/329,183, filed on Oct. 12, 2001.

(51) Int. Cl.
*A61K 38/00* (2006.01)
*A61K 38/12* (2006.01)

(52) U.S. Cl. ........................ 530/300; 530/317
(58) Field of Classification Search ............... None
See application file for complete search history.

(56) References Cited

U.S. PATENT DOCUMENTS

| | | | |
|---|---|---|---|
| 5,620,675 A * | 4/1997 | McBride et al. | 424/1.69 |
| 5,910,583 A | 6/1999 | Marks et al. | |
| 5,922,845 A | 7/1999 | Deo et al. | |
| 6,015,567 A | 1/2000 | Hudziak et al. | |
| 6,074,640 A | 6/2000 | Curiel et al. | |
| 6,123,939 A | 9/2000 | Shawver et al. | |
| 6,165,464 A | 12/2000 | Hudziak et al. | |
| 6,358,525 B1 * | 3/2002 | Guo et al. | 424/464 |
| 6,417,168 B1 | 7/2002 | Greene et al. | |
| 6,723,694 B1 | 4/2004 | Ben-Sasson | |
| 2003/0171278 A1 * | 9/2003 | Dennis | 514/12 |

FOREIGN PATENT DOCUMENTS

WO    WO 03/061559 A2    7/2003

OTHER PUBLICATIONS

GENBANK Accession No. AAA75493. HER2 receptor (*Homo sapiens*) Sep. 18, 1995.
Aasland, R., et al. "Expression of oncogenes in thyroid tumours: coexpression of c-erbB2/neu and c-erbB." *Br J Cancer*. Apr. 1988;57(4):358-63. Abstract Only.
Allan, SM., et al., "Radioimmunolocalisation in breast cancer using the gene product of c-erbB2 as the target antigen." *Br J Cancer*. Apr. 1993;67(4):706-12. Abstract Only.
Arap, W., et al., "Cancer treatment by targeted drug delivery to tumor vasculature in a mouse model." *Science*, 279:377-380. (1998).

(Continued)

*Primary Examiner*—Larry H. Helms
*Assistant Examiner*—Hong Sang
(74) *Attorney, Agent, or Firm*—Wolf, Greenfield & Sacks, P.C.

(57) ABSTRACT

The invention provides methods and compositions for diagnosing and treating subjects using EBPs. Specifically disclosed are peptides and peptidomimetics that bind selectively to the extracellular domain of ErbB2. These compositions are useful in the prevention and treatment of disorders characterized by ErbB2 overexpression (e.g., breast cancer).

9 Claims, 9 Drawing Sheets

OTHER PUBLICATIONS

Braun, S., et al., ErbB2 overexpression on occult metastic cells in bone marrow predicts poor clinical outcome of stage I-III breast cancer patients. *Cancer Res.* Mar. 1, 2001;61(5):1890-5. Abstract Only.

Carraway, et al., Multiple facets of sialomucin complex/MUC4, a membrane mucin and erbb2 ligand, in tumors and tissues (Y2K update). *Front Biosci.* Jan. 1, 2000;5:D95-D107. Abstract Only.

Cell Signaling Technology, Inc., HER2/ErbB2 Antibody #2242 product data sheet. 3 pages. Updated Sep. 21, 2001 from cellsignal.com.

Garratt, AN, et al., Neuregulin, a factor with many functions in the life of a schwann cell. *Bioessays.* Nov. 2000;22(11):987-96. Abstract Only.

GENBANK Accession No. M11730 Human tyrosine kinase-type receptor (HER2) mRNA, complete cds. Sep. 18, 1995.

GENBANK Accession No. X03363, Human c-erb-B-2 mRNA. Mar. 30, 1995.

GENENTECH, Inc., Herceptin® (trastu zumab) Full Prescribing information. 15 pages. Revised Sep. 2000.

Harari, D., et al., Molecular mechanisms underlying ErbB2/HER2 action in breast cancer. *Oncogene.* Dec. 11, 2000;19(53):6102-14. Abstract Only.

Hijazi, et al., Heregulin regulates the actin cytoskeleton and promotes invasive properties in breast cancer cell lines. *Int J Oncol.* Oct. 2000;17(4):629-41. Abstract Only.

Huang, G., et al., "Overexpression of ErbB2 impairs ligand-dependent downregulation of epidermal growth factor receptors via a post-transcriptional mechanism." *J Cell Biochem.* Jul. 1, 1999;74(1):23-30. Abstract Only.

Jardines, L. et al., neu(c-erbB-2/HER2) and the epidermal growth factor receptor (EGFR) in breast cancer. *Pathobiology.* 1993;61(5-6):268-82. Abstract Only.

Johannessen, Le, et al., Heterodimerization of the epidermal-growth-factor (EGF) receptor and ErbB2 and the affinity of EGF binding are regulated by different mechanisms. *Biochem J.* May 15, 2001;356(Pt I):87-96. Abstract Only.

Komatsu, M., et al., Muc4/sialomucin complex, an intramembrane modulator of ErbB2/HER2/Neu, potentiates primary tumor growth and suppresses apoptosis in a xenotransplanted tumor. *Oncogene.* Jan. 25, 2001;20(4):461-70. Abstract Only.

Krag, D., et al., "Identification of small peptide ligands to ErbB2." Department of Defense Era of Hope Meeting, Sep. 25-28, 2002. Orlando, FL. Poster Session Abstract P52-8.

Krag, D., et al., "Phage-displayed random peptide libraries in mice. Toxicity after serial panning." Department of Defense Era of Hope Meeting, Sep. 25-28, 2002. Orlando, FL. Poster Session Abstract P52-9.

Kumar, R., et al., New insights into anti-HER-2 receptor monoclonal antibody research. *Semin Oncol.* Dec. 2000;27(6 Suppl 11):84-91; discussion 92-100. Abstract Only.

Lupu, R., et al., William L. McGuire Memorial Symposium. The role of erbB2 signal transduction pathways in human breast cancer. *Breast Cancer Res Treat.* 1993;27(1-2):83-93. Abstract Only.

Menard, S., et al., Role of HER2 gene overexpression in breast carcinoma. *J Cell Physiol.* Feb. 2000;182(2):150-62. Abstract Only.

Nagy, P., et al., Complexity of signal transduction mediated by ErbB2: clues to the potential of receptor-targeted cancer therapy. *Pathol Oncol Res.* 1999;5(4):255-71. Abstract Only.

Natali, PG et al., "Expression of the p185 encoded by HER2 oncogene in normal and transformed human tissues." *Int J Cancer.* Mar. 15, 1990;45(3):457-61. Abstract Only.

Oligino, L., et al., (1997) "Nonphosphorylated peptide ligands for the Grb2 Src homology 2 domain." *J. Biol. Chem.* 272(46):29046-29052.

Ouyang, X., et al., Association of ErbB2 Ser1113 phosphorylation with epidermal growth factor receptor co-expression and poor prognosis in human breast cancer. *Mol Cell Biochem.* Feb. 2001;218(1-2):47-54. Abstract Only.

Park, B-W., et al., (2000) "Rationally designed anti-HER2/neu peptide mimetic disables P185HER2/neu tyrosine kinases in vitro and in vivo." *Nat Biotechnol.* 18(2):194-8.

Pegram, M., et al., Biological rationale for HER2/neu (c-erbB2) as a target for monoclonal antibody therapy. *Semin Oncol.* Oct. 2000;27(5 Suppl 9):13-9. Abstract Only.

Porcelli, B., et al., Expression of p185 and p53 in benign and malignant colorectal lesions. *Histochem J.* Jan. 2001;33(1):51-7. Abstract Only.

Riviere, A., et al., "Expression of c-erbB2 and c-myc in squamous epithelia and squamous cell carcinomas of the head and neck and the lower female genital tract." *J Oral Pathol Med* Oct. 1990;19(9):408-13. Abstract Only.

Schier R, et al., "In vitro and in vivo characterization of a human anti-c-erbB-2 single-chain Fv isolated from a filamentous phage antibody library." *Immunotechnology* May 1995;1(1):73-81. Abstract and selected pages from article (pp. 77, 80-81).

Schier R, et al., "Isolation of picomolar affinity anti-c-erbB-2 single-chain Fv by molecular evolution of the complementarity determining regions in the center of the antibody binding site." *J Mol Biol* Nov. 8, 1996;263(4):551-67. Abstract and article.

Weinstein, EJ, et al. The extracellular region of heregulin is sufficient to promote mammary gland proliferation and tumorigenesis but not apoptosis. *Cancer Res.* Jul. 15, 2000;60(14):3856-61. Abstract Only.

Zajchowski D, et al., "Expression of growth factors and oncogenes in normal and tumor-derived human mammary epithelial cells." *Cancer Res* Dec. 15, 1988;48(24 Pt I):7041-7. Abstract Only.

\* cited by examiner

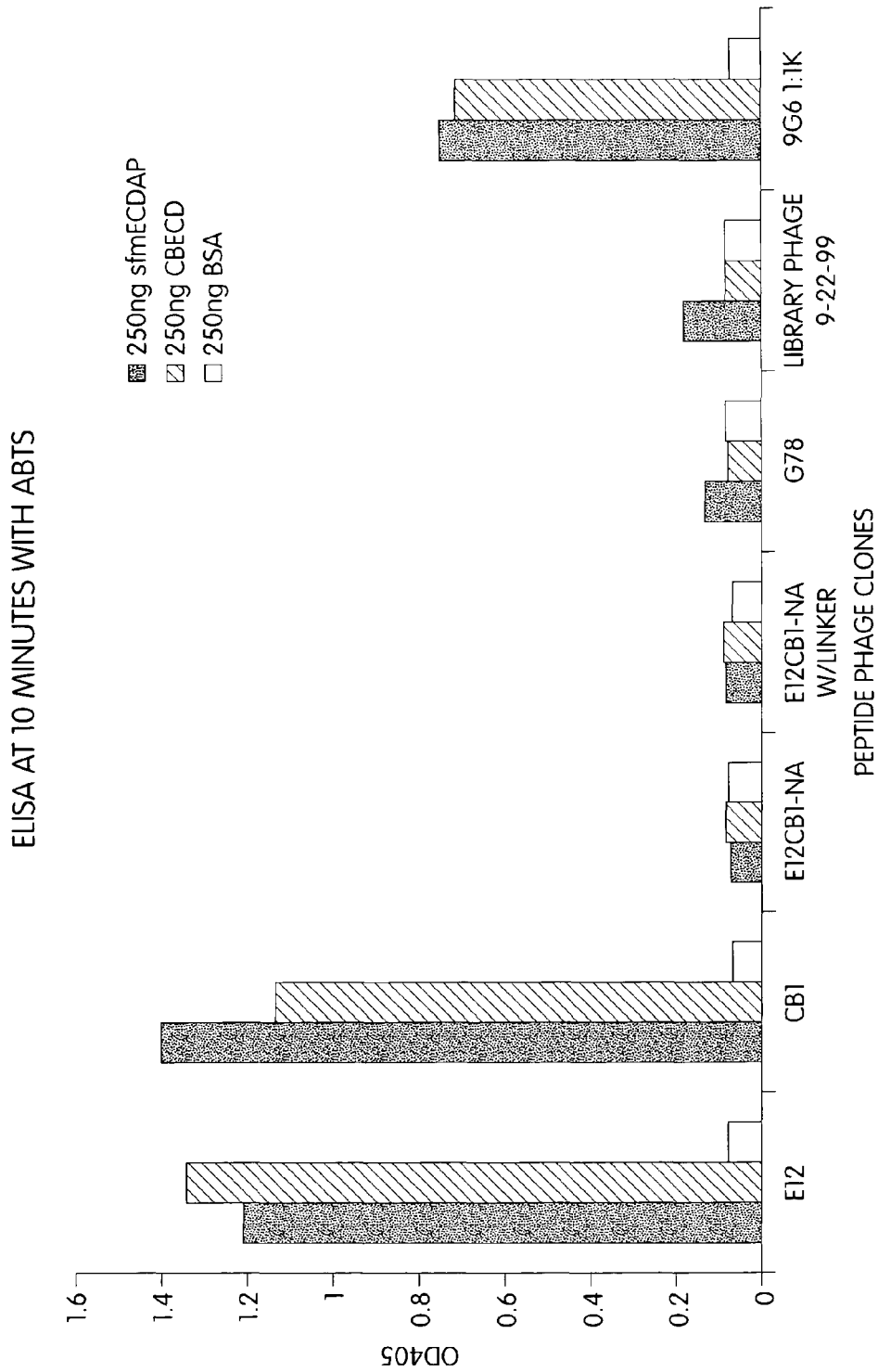

SEQUENCE LISTING

```
<160> NUMBER OF SEQ ID NOS: 46

<210> SEQ ID NO 1
<211> LENGTH: 20
<212> TYPE: PRT
<213> ORGANISM: Artificial sequence
<220> FEATURE:
<223> OTHER INFORMATION: Synthetic peptide

<400> SEQUENCE: 1

Trp Thr Gly Trp Cys Leu Asn Pro Glu Glu Ser Thr Trp Gly Phe Cys
1               5                   10                  15

Thr Gly Ser Phe
            20

<210> SEQ ID NO 2
<211> LENGTH: 19
<212> TYPE: PRT
<213> ORGANISM: Artificial sequence
<220> FEATURE:
<223> OTHER INFORMATION: Synthetic peptide

<400> SEQUENCE: 2

Val Val Ala Cys Ser Trp Asp Trp Thr Met Gly Ala Val Val Cys Tyr
1               5                   10                  15

Glu Arg Ile

<210> SEQ ID NO 3
<211> LENGTH: 20
<212> TYPE: PRT
<213> ORGANISM: Artificial sequence
<220> FEATURE:
<223> OTHER INFORMATION: Synthetic peptide

<400> SEQUENCE: 3

Gly Phe Trp Thr Cys Glu Tyr Asp Trp Trp Ser Asp Ala Thr Val Cys
1               5                   10                  15

Met His Thr Leu
            20
```

```
<210> SEQ ID NO 4
<211> LENGTH: 20
<212> TYPE: PRT
<213> ORGANISM: Artificial sequence
<220> FEATURE:
<223> OTHER INFORMATION: Synthetic peptide

<400> SEQUENCE: 4

Gly Arg Gly Trp Cys Trp Ser Glu Trp Gln Asn Asp Trp Phe Trp Cys
1               5                   10                  15

Trp Asp Val Trp
            20

<210> SEQ ID NO 5
<211> LENGTH: 20
<212> TYPE: PRT
<213> ORGANISM: Artificial sequence
<220> FEATURE:
<223> OTHER INFORMATION: Synthetic peptide

<400> SEQUENCE: 5

Trp Thr Gly Trp Cys Leu Asn Pro Glu Glu Ser Thr Trp Gly Phe Cys
1               5                   10                  15

Thr Gly Ser Phe
            20

<210> SEQ ID NO 6
<211> LENGTH: 20
<212> TYPE: PRT
<213> ORGANISM: Artificial sequence
<220> FEATURE:
<223> OTHER INFORMATION: Synthetic peptide

<400> SEQUENCE: 6

Ala Arg Leu Gln Cys Trp Ser Leu Gly Trp Gly Gly Pro Val Tyr Cys
1               5                   10                  15

Gly Phe Gly Gln
            20

<210> SEQ ID NO 7
<211> LENGTH: 20
<212> TYPE: PRT
<213> ORGANISM: Artificial sequence
<220> FEATURE:
<223> OTHER INFORMATION: Synthetic peptide

<400> SEQUENCE: 7

Ile Gln Glu Val Cys Trp Phe Asp Tyr Asn Leu Ser Gln Trp His Cys
1               5                   10                  15

Met Thr Val Ile
            20

<210> SEQ ID NO 8
<211> LENGTH: 20
<212> TYPE: PRT
<213> ORGANISM: Artificial sequence
<220> FEATURE:
<223> OTHER INFORMATION: Synthetic peptide

<400> SEQUENCE: 8

Pro Asp Ile Tyr Cys Leu Ser Val Thr Ala Pro Gly Phe Leu Ile Cys
1               5                   10                  15

Tyr Glu Arg Tyr
```

-continued

```
            20

<210> SEQ ID NO 9
<211> LENGTH: 20
<212> TYPE: PRT
<213> ORGANISM: Artificial sequence
<220> FEATURE:
<223> OTHER INFORMATION: Synthetic peptide

<400> SEQUENCE: 9

His Asp Glu Leu Cys Val Phe Ser Phe Asp Phe Asn Ala Leu Leu Cys
1               5                   10                  15

Trp Pro Ala Glu
            20

<210> SEQ ID NO 10
<211> LENGTH: 20
<212> TYPE: PRT
<213> ORGANISM: Artificial sequence
<220> FEATURE:
<223> OTHER INFORMATION: Synthetic peptide

<400> SEQUENCE: 10

Leu Asn Trp Glu Cys Trp Tyr Asp Tyr Arg Leu Glu Ala Trp Asp Cys
1               5                   10                  15

Arg Gly Asp Ile
            20

<210> SEQ ID NO 11
<211> LENGTH: 11
<212> TYPE: PRT
<213> ORGANISM: Artificial sequence
<220> FEATURE:
<223> OTHER INFORMATION: Synthetic peptide

<400> SEQUENCE: 11

Cys Glu Val Trp Gly Glu Val Pro Trp Thr Cys
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic peptide

<400> SEQUENCE: 12

Cys Glu Val Trp Gly Phe Val Pro Trp Ala Cys
1               5                   10

<210> SEQ ID NO 13
<211> LENGTH: 20
<212> TYPE: PRT
<213> ORGANISM: Artificial sequence
<220> FEATURE:
<223> OTHER INFORMATION: Synthetic peptide

<400> SEQUENCE: 13

Ser Asn Glu Ser Cys Gly Ser Pro Ile Asn Pro Trp Gly Glu Met Cys
1               5                   10                  15

Leu Leu Met Leu
            20

<210> SEQ ID NO 14
<211> LENGTH: 57
```

<212> TYPE: DNA
<213> ORGANISM: Artificial sequence
<220> FEATURE:
<223> OTHER INFORMATION: Synthetic oligonucleotide

<400> SEQUENCE: 14
actggttggt gtttaaatcc tgaagaatct acttggggtt tttgtactgg ttctttt        57

<210> SEQ ID NO 15
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 15
gttgttgcat gttcttggga ttggactatg ggtgcagttg tttgttatga acgtatt        57

<210> SEQ ID NO 16
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 16 ggttttgga cttgtgaata tgattggtgg tctgatgcaa ctgtttgtat gcatacttta     60

<210> SEQ ID NO 17
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 17
ggtcgtggtt ggtgttggtc tgaatggcaa aatgattggt tttggtgttg ggatgtttgg     60

<210> SEQ ID NO 18
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 18
tggactggtt ggtgtttaaa tcctgaagaa tctacttggg gttttgtac tggttctttt     60

<210> SEQ ID NO 19
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 19
gcacgtttac aatgttggtc tttaggttgg ggtggtcctg tttattgtgg ttttggtcaa     60

<210> SEQ ID NO 20
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 20
attcaagaag tttgttggtt tgattataat ttatctcaat ggcattgtat gactgttatt    60

<210> SEQ ID NO 21
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 21
cctgatattt attgtttatc tgttactgca cctggttttt taatttgtta tgaacgttat    60

<210> SEQ ID NO 22
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 22
catgatgaat tatgtgtttt ttcttttgat tttaatgcat tattatgttg gcctgcagaa    60

<210> SEQ ID NO 23
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 23
ttaaattggg aatgttggta tgattatcgt ttagaagcat gggattgtcg tggtgatatt    60

<210> SEQ ID NO 24
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 24
tgtgaagttt ggggtgaagt tccttggact tgt                                 33

<210> SEQ ID NO 25
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 25
tgtgaagttt gggttttgt tccttgggca tgt                                  33

<210> SEQ ID NO 26
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 26
tctaatgaat cttgtggttc tcctattaat ccttggggtg aaatgtgttt attaatgtta    60

<210> SEQ ID NO 27
<211> LENGTH: 4530
<212> TYPE: DNA
<213> ORGANISM: Homo sapiens

<400> SEQUENCE: 27

```
aattctcgag ctcgtcgacc ggtcgacgag ctcgagggtc gacgagctcg agggcgcgcg      60
cccggccccc acccctcgca gcaccccgcg ccccgcgccc tcccagccgg gtccagccgg     120
agccatgggg ccggagccgc agtgagcacc atggagctgg cggccttgtg ccgctggggg     180
ctcctcctcg ccctcttgcc ccccggagcc gcgagcaccc aagtgtgcac ggcacagac      240
atgaagctgc ggctccctgc cagtcccgag acccacctgg acatgctccg ccacctctac     300
cagggctgcc aggtggtgca gggaaacctg gaactcacct acctgcccac caatgccagc     360
ctgtccttcc tgcaggatat ccaggaggtg cagggctacg tgctcatcgc tcacaaccaa     420
gtgaggcagg tcccactgca gaggctgcgg attgtgcgag cacccagct ctttgaggac      480
aactatgccc tggccgtgct agacaatgga gaccgctga caataccac ccctgtcaca       540
ggggcctccc caggaggcct gcgggagctg cagcttcgaa gcctcacaga gatcttgaaa     600
ggagggtct tgatccagcg gaaccccag ctctgctacc aggacacgat tttgtggaag       660
gacatcttcc acaagaacaa ccagctggct ctcacactga tagacaccaa ccgctctcgg     720
gcctgccacc cctgttctcc gatgtgtaag ggctcccgct gctggggaga gagttctgag     780
gattgtcaga gcctgacgcg cactgtctgt gccggtggct gtgcccgctg caaggggcca     840
ctgcccactg actgctgcca tgagcagtgt gctgccggct gcacgggccc caagcactct     900
gactgcctgg cctgcctcca cttcaaccac agtggcatct gtgagctgca ctgcccagcc     960
ctggtcacct acaacacaga cacgtttgag tccatgccca tcccgagggg ccggtataca    1020
ttcggcgcca gctgtgtgac tgcctgtccc tacaactacc tttctacgga cgtgggatcc    1080
tgcacctcg tctgccccct gcacaaccaa gaggtgacag cagaggatgg aacacagcgg     1140
tgtgagaagt gcagcaagcc ctgtgcccga gtgtgctatg gtctgggcat ggagcacttg    1200
cgagaggtga gggcagttac cagtgccaat atccaggagt tgctggctg caagaagatc     1260
tttgggagcc tggcatttct gccggagagc tttgatgggg acccagcctc caacactgcc    1320
ccgctccagc cagagcagct ccaagtgttt gagactctgg aagagatcac aggttaccta    1380
tacatctcag catggccgga cagcctgcct gacctcagcg tcttccagaa cctgcaagta    1440
atccggggac gaattctgca caatggcgcc tactcgctga ccctgcaagg gctgggcatc    1500
agctggctgg ggctgcgctc actgagggaa ctgggcagtg gactggccct catccaccat    1560
aacacccacc tctgcttcgt gcacacggtg ccctgggacc agctctttcg gaacccgcac    1620
caagctctgc tccacactgc caaccggcca gaggacgagt gtgtgggcga gggcctggcc    1680
tgccaccagc tgtgcgcccg agggcactgc tgggtccag gcccacccca gtgtgtcaac    1740
tgcagccagt tccttcgggg ccaggagtgc gtggaggaat gccgagtact gcaggggctc    1800
cccagggagt atgtgaatgc caggcactgt ttgccgtgcc accctgagtg tcagccccag    1860
aatggctcag tgacctgttt tggaccggag gctgaccagt gtgtggcctg tgcccactat    1920
aaggaccctc ccttctgcgt ggcccgctgc cccagcggtg tgaaacctga cctctcctac    1980
atgcccatct ggaagtttcc agatgaggag ggcgcatgcc agccttgccc catcaactgc    2040
acccactcct gtgtggacct ggatgacaag ggctgccccg ccgagcagag agccagccct    2100
ctgacgtcca tcgtctctgc ggtggttggc attctgctgg tcgtggtctt ggggtggtc    2160
tttgggatcc tcatcaagcg acggcagcag aagatccgga agtacacgat gcggagactg    2220
ctgcaggaaa cggagctggt ggagccgctg acacctagcg gagcgatgcc caaccaggcg    2280
```

-continued

```
cagatgcgga tcctgaaaga dacggagctg aggaaggtga aggtgcttgg atctggcgct    2340
tttggcacag tctacaaggg catctggatc cctgatgggg agaatgtgaa aattccagtg    2400
gccatcaaag tgttgaggga aaacacatcc cccaaagcca acaaagaaat cttagacgaa    2460
gcatacgtga tggctggtgt gggctcccca tatgtctccc gccttctggg catctgcctg    2520
acatccacgg tgcagctggt gacacagctt atgccctatg ctgcctctt agaccatgtc     2580
cgggaaaacc gcggacgcct gggctcccag gacctgctga actggtgtat gcagattgcc    2640
aaggggatga gctacctgga ggatgtgcgg ctcgtacaca gggacttggc cgctcggaac    2700
gtgctggtca gagtcccaa ccatgtcaaa attacagact tcgggctggc tcggctgctg     2760
gacattgacg agacagagta ccatgcagat gggggcaagg tgcccatcaa gtggatggcg    2820
ctggagtcca ttctccgccg gcggttcacc caccagagtg atgtgtggag ttatggtgtg    2880
actgtgtggg agctgatgac ttttggggcc aaaccttacg atgggatccc agcccgggag    2940
atccctgacc tgctggaaaa gggggagcgg ctgccccagc cccccatctg caccattgat    3000
gtctacatga tcatggtcaa atgttggatg attgactctg aatgtcggcc aagattccgg    3060
gagttggtgt ctgaattctc ccgcatggcc agggaccccc agcgctttgt ggtcatccag    3120
aatgaggact gggcccagc cagtcccttg gacagcacct tctaccgctc actgctggag     3180
gacgatgaca tgggggacct ggtggatgct gaggagtatc tggtacccca gcagggcttc    3240
ttctgtccag accctgcccc gggcgctggg ggcatggtcc accacaggca ccgcagctca    3300
tctaccagga gtggcggtgg ggacctgaca ctagggctgg agccctctga agaggaggcc    3360
cccaggtctc cactggcacc ctccgaaggg gctggctccg atgtatttga tggtgacctg    3420
ggaatggggg cagccaaggg gctgcaaagc ctccccacac atgacccag ccctctacag     3480
cggtacagtg aggaccccac agtacccctg ccctctgaga ctgatggcta cgttgccccc    3540
ctgacctgca gcccccagcc tgaatatgtg aaccagccag atgttcggcc ccagcccct    3600
tcgcccccgag agggccctct gcctgctgcc cgacctgctg gtgccactct ggaaagggcc    3660
aagactctct cccagggaa gaatgggtc gtcaaagacg ttttttgcctt tgggggtgcc     3720
gtggagaacc ccgagtactt gacaccccag ggaggagctg ccctcagcc ccaccctcct     3780
cctgccttca gcccagcctt cgacaacctc tattactggg accaggaccc accagagcgg    3840
ggggctccac ccagcacctt caaagggaca cctacggcag agaacccaga gtacctgggt    3900
ctggacgtgc cagtgtgaac cagaaggcca agtccgcaga agccctgatg tgtcctcagg    3960
gagcagggaa ggcctgactt ctgctggcat caagaggtgg gagggccctc cgaccacttc    4020
cagggggaacc tgccatgcca ggaacctgtc ctaaggaacc ttccttcctg cttgagttcc    4080
cagatggctg gaagggtcc agcctcgttg aagaggaac agcactgggg agtctttgtg      4140
gattctgagg ccctgcccaa tgagactcta gggtccagtg gatgccacag cccagcttgg    4200
ccctttcctt ccagatcctg ggtactgaaa gccttaggga agctggcctg agaggggaag    4260
cggccctaag ggagtgtcta agaacaaaag cgacccattc agagactgtc cctgaaacct    4320
agtactgccc cccatgagga aggaacagca atggtgtcag tatccaggct ttgtacagag    4380
tgcttttctg tttagttttt acttttttg ttttgttttt ttaaagacga aataaagacc      4440
caggggagaa tgggtgttgt atgggagggc aagtgtgggg ggtccttctc cacacccact    4500
ttgtccattt gcaaatatat tttggaaaac                                     4530
```

<210> SEQ ID NO 28
<211> LENGTH: 1255

```
<212> TYPE: PRT
<213> ORGANISM: Homo sapiens

<400> SEQUENCE: 28

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400
```

```
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Val Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
```

-continued

```
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
            835                 840                 845
Arg Asn Val Leu Val Lys Ser Pro Asn His Val Lys Ile Thr Asp Phe
    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
            915                 920                 925
Arg Glu Ile Pro Asp Leu Leu Glu Lys Gly Glu Arg Leu Pro Gln Pro
    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
            995                 1000                1005
Leu Glu Asp Asp Asp Met Gly Asp Leu Val Asp Ala Glu Glu Tyr
    1010                1015                1020
Leu Val Pro Gln Gln Gly Phe Phe Cys Pro Asp Pro Ala Pro Gly
    1025                1030                1035
Ala Gly Gly Met Val His His Arg His Arg Ser Ser Ser Thr Arg
    1040                1045                1050
Ser Gly Gly Gly Asp Leu Thr Leu Gly Leu Glu Pro Ser Glu Glu
    1055                1060                1065
Glu Ala Pro Arg Ser Pro Leu Ala Pro Ser Glu Gly Ala Gly Ser
    1070                1075                1080
Asp Val Phe Asp Gly Asp Leu Gly Met Gly Ala Ala Lys Gly Leu
    1085                1090                1095
Gln Ser Leu Pro Thr His Asp Pro Ser Pro Leu Gln Arg Tyr Ser
    1100                1105                1110
Glu Asp Pro Thr Val Pro Leu Pro Ser Glu Thr Asp Gly Tyr Val
    1115                1120                1125
Ala Pro Leu Thr Cys Ser Pro Gln Pro Glu Tyr Val Asn Gln Pro
    1130                1135                1140
Asp Val Arg Pro Gln Pro Pro Ser Pro Arg Glu Gly Pro Leu Pro
    1145                1150                1155
Ala Ala Arg Pro Ala Gly Ala Thr Leu Glu Arg Ala Lys Thr Leu
    1160                1165                1170
Ser Pro Gly Lys Asn Gly Val Val Lys Asp Val Phe Ala Phe Gly
    1175                1180                1185
Gly Ala Val Glu Asn Pro Glu Tyr Leu Thr Pro Gln Gly Gly Ala
    1190                1195                1200
Ala Pro Gln Pro His Pro Pro Ala Phe Ser Pro Ala Phe Asp
    1205                1210                1215
Asn Leu Tyr Tyr Trp Asp Gln Asp Pro Pro Glu Arg Gly Ala Pro
```

```
            1220                1225                1230
Pro Ser   Thr Phe Lys Gly Thr   Pro Thr Ala Glu Asn   Pro Glu Tyr
            1235                1240                1245

Leu Gly   Leu Asp Val Pro Val
            1250                1255

<210> SEQ ID NO 29
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(4)
<223> OTHER INFORMATION: Xaa = any amino acid

<400> SEQUENCE: 29

Xaa Xaa Xaa Xaa Cys Leu Asn Pro Glu Glu Ser Thr Trp Gly Phe Cys
1               5                   10                  15

Arg Ser Ala Gly
            20

<210> SEQ ID NO 30
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (6)..(10)
<223> OTHER INFORMATION: Xaa = any amino acid

<400> SEQUENCE: 30

Trp Thr Gly Trp Cys Xaa Xaa Xaa Xaa Xaa Ser Thr Trp Gly Phe Cys
1               5                   10                  15

Arg Ser Ala Gly
            20

<210> SEQ ID NO 31
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(15)
<223> OTHER INFORMATION: Xaa = any amino acid

<400> SEQUENCE: 31

Trp Thr Gly Trp Cys Leu Asn Pro Glu Glu Xaa Xaa Xaa Xaa Xaa Cys
1               5                   10                  15

Arg Ser Ala Gly
            20

<210> SEQ ID NO 32
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (17)..(21)
<223> OTHER INFORMATION: Xaa = any amino acid
```

<400> SEQUENCE: 32

Trp Thr Gly Trp Cys Leu Asn Pro Glu Glu Ser Thr Trp Gly Phe Cys
1               5                   10                  15

Xaa Xaa Xaa Xaa Xaa
            20

<210> SEQ ID NO 33
<211> LENGTH: 20
<212> TYPE: PRT
<213> ORGANISM: Artificial sequence
<220> FEATURE:
<223> OTHER INFORMATION: Synthetic peptide

<400> SEQUENCE: 33

Trp Thr Gly Trp Cys Leu Asn Pro Glu Glu Ser Thr Trp Gly Phe Cys
1               5                   10                  15

Arg Ser Ala Gly
            20

<210> SEQ ID NO 34
<211> LENGTH: 20
<212> TYPE: PRT
<213> ORGANISM: Artificial sequence
<220> FEATURE:
<223> OTHER INFORMATION: Synthetic peptide

<400> SEQUENCE: 34

Trp Thr Gly Trp Cys Leu Ser Pro Glu Ser Thr Trp Gly Phe Cys
1               5                   10                  15

Arg Ser Ala Gly
            20

<210> SEQ ID NO 35
<211> LENGTH: 20
<212> TYPE: PRT
<213> ORGANISM: Artificial sequence
<220> FEATURE:
<223> OTHER INFORMATION: Synthetic peptide

<400> SEQUENCE: 35

Trp Thr Gly Trp Cys Leu Asn Pro Glu Glu Ser Thr Trp Gly Phe Cys
1               5                   10                  15

Ser Gly Tyr Ile
            20

<210> SEQ ID NO 36
<211> LENGTH: 20
<212> TYPE: PRT
<213> ORGANISM: Artificial sequence
<220> FEATURE:
<223> OTHER INFORMATION: Synthetic peptide

<400> SEQUENCE: 36

Trp Thr Gly Trp Cys Phe Asp Asp Asn His Ser Thr Trp Gly Phe Cys
1               5                   10                  15

Thr Gly Ser Phe
            20

<210> SEQ ID NO 37
<211> LENGTH: 20
<212> TYPE: PRT
<213> ORGANISM: Artificial sequence
<220> FEATURE:

-continued

<223> OTHER INFORMATION: Synthetic peptide

<400> SEQUENCE: 37

Asp Thr Asp Met Cys Trp Trp Trp Ser Arg Glu Phe Gly Trp Glu Cys
1               5                   10                  15

Ala Gly Ala Gly
        20

<210> SEQ ID NO 38
<211> LENGTH: 20
<212> TYPE: PRT
<213> ORGANISM: Artificial sequence
<220> FEATURE:
<223> OTHER INFORMATION: Synthetic peptide

<400> SEQUENCE: 38

Ser Leu Ala Leu Cys Leu Ser Glu Gly Val Leu Leu Gly Ala Asp Cys
1               5                   10                  15

Arg Val Leu Phe
        20

<210> SEQ ID NO 39
<211> LENGTH: 20
<212> TYPE: PRT
<213> ORGANISM: Artificial sequence
<220> FEATURE:
<223> OTHER INFORMATION: Synthetic peptide

<400> SEQUENCE: 39

Trp Ser Ser Met Cys Gly Asp Pro Thr Ile Ala Asp Trp Leu Trp Cys
1               5                   10                  15

Phe Ser Asp Ala
        20

<210> SEQ ID NO 40
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 40
tggactggtt ggtgtttaaa tcctgaagaa tctacttggg gttttttgtcg ttctgcaggt      60

<210> SEQ ID NO 41
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 41
tggactggtt ggtgtttatc tcctgaagaa tctacttggg gttttttgtcg ttctgcaggt      60

<210> SEQ ID NO 42
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 42
tggactggtt ggtgtttaaa tcctgaagaa tctacttggg gttttttgttc tggttatatt      60

```
<210> SEQ ID NO 43
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 43
tggactggtt ggtgttttga tgataatcat tctacttggg gtttttgtac tggttctttt     60

<210> SEQ ID NO 44
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 44
gatactgata tgtgttggtg gtggtctcgt gaatttggtt gggaatgtgc aggtgcaggt     60

<210> SEQ ID NO 45
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 45
tctttagcat tatgtttatc tgaaggtgtt ttattaggtg cagattgtcg tgttttattt     60

<210> SEQ ID NO 46
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 46
tggtcttcta tgtgtggtga tcctactatt gcagattggt tatggtgttt ttctgatgca     60
```

US 7,098,302 B2

BINDING PEPTIDES SPECIFIC FOR THE EXTRACELLULAR DOMAIN OF ERBB2 AND USES THEREFOR

RELATED APPLICATIONS

This application claims priority to U.S. Provisional Patent Application filed Oct. 12, 2001 entitled "BINDING PEPTIDES SPECIFIC FOR THE EXTRACELLULAR DOMAIN OF ERBB2 AND USES THEREFOR", Ser. No. 60/329,183, the contents of which are incorporated by reference herein in their entirety.

GOVERNMENT SUPPORT

This work was funded in part by grant number 1 R01 CA80790-01, from the National Institutes of Health, and grant number DAMD17-94-J-4373 from the Department of Defense. Accordingly, the United States Government may have certain rights to this invention.

FIELD OF THE INVENTION

The invention relates to peptides and peptidomimetics that bind to the extracellular domain of ErbB2, and their use in diagnosis, prevention and treatment of disorders associated with overexpression of ErbB2 (e.g., breast cancer).

BACKGROUND OF THE INVENTION

One major drawback of most cancer therapeutics is the lack of specificity and associated toxicity to normal tissues. A significant advance in therapeutic effectiveness would be likely achieved if cytotoxic agents could be delivered specifically to tumor cells, with minimal delivery to normal tissue. Conjugation of cytotoxic agents to molecules that bind specifically to a tumor target found would then enable tumor-specific delivery and would reduce non-specific toxicity.

Molecules that are found specifically on the surface of cancer cells are especially promising targets for tumor-specific homing molecules. An example of such a cell surface molecule is ErbB2 (also known as HER2 or neu). ErbB2 is a member of the ErbB family of growth factor receptors, which includes ErbB1 (also known as epidermal growth factor receptor). ErbB2 is a membrane protein containing a cysteine-rich extracellular domain (ECD), a transmembrane domain, and an intracellular tyrosine kinase domain. It is overexpressed on the surface of breast cancer cells in approximately 30% of newly diagnosed patients and is associated with a poor prognosis. Importantly, metastatic tumor cells in the bone marrow of 60–70% of breast cancer patients overexpress ErbB2 on their surface (Pantel et al., J Natl Cancer Inst 85:1419; Braun et al., Cancer Research, 61:1890). Therefore, ErbB2 is an extremely promising target molecule for some forms of cancer.

SUMMARY OF THE INVENTION

The invention relates to the identification of peptides that specifically bind to the extracellular domain of ErbB2. ErbB2 overexpression is a hallmark of many forms of cancer, including most notably breast cancer, ovarian cancer, stomach cancer, lung cancer and bladder cancer, among others. Accordingly, the discovery of small, preferably peptide, molecules that bind to ErbB2 facilitates detection, prevention and treatment of disorders characterized by overexpression of ErbB2 (including those that overexpress ErbB2), such as those listed above. Prior to the invention, an antibody to ErbB2 (i.e., Herceptin) had been identified, and tested clinically. The small peptides of the present invention have pharmacokinetic properties superior to larger molecules such as antibodies.

Accordingly, in one aspect, the invention provides ErbB2 binding peptides, referred to herein as EBP. The invention provides at least 20 EBP, the sequences of which are provided below. Some of the EBP of the invention share common sequence elements. In preferred embodiments, the EBP of the invention bind to the extracellular domain of ErbB2. The EBP include both the peptides described herein as well as their functional equivalents. In preferred embodiments, the functional equivalents are peptides that have at least 50%, at least 60%, at least 70%, at least 80%, at least 90%, or at least 95% identity with the peptides described herein. The functional equivalents may be different from the peptides described herein at one, two, three, four, or more amino acid positions. In the most common instances, such differences will involve conservative amino acid substitutions.

Thus, in one aspect, the invention provides a composition comprising a peptide comprising an amino acid sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:33, SEQ ID NO:34, SEQ ID NO:35, SEQ ID NO:36, SEQ ID NO:37, SEQ ID NO:38 and SEQ ID NO:39, and functional equivalents thereof, including functionally equivalent fragments thereof. These peptides are referred to herein as ErbB2-binding peptides (i.e., EBP), and each is designated with a unique number (e.g., EBP-1, EBP-2, EBP-3, EBP-4, EBP-5, EBP-6, EBP-7, EBP-8, EBP-9, EBP-10, EBP-11, EBP-12, EBP-13, etc.). As indicated in the Brief Description of the Sequence Listing, SEQ ID NO:1 through to SEQ ID NO:13 and SEQ ID NO:33 through to SEQ ID NO:39 represent the amino acid sequences of EBP-1 through to EBP-13 and EBP-14 through to EBP-20, respectively.

In one embodiment, the EBP is cyclic or is capable of being cyclized via, for example, a disulfide bond, a thioether linkage or a peptide bond. In another embodiment, the peptide is conjugated to an agent. The agent may be selected from the group consisting of a toxin, a radioactive molecule, a detectable label, an imaging agent, a diagnostic agent, a chemotherapeutic agent, an anti-angiogenic agent, an anti-cancer agent, an immunomodulatory agent, an antigen or antigenic moiety, an apoptosis agent, and a translocating agent. The translocating agent can be used to translocate the peptide or preferably a therapeutic agent attached to the peptide into the cell in order to deliver the therapeutic agent to the cell. In another embodiment, the peptide is used together with an agent that functions in the cytoplasmic compartment of a cell, such as for example an agent that inhibits the cytoskeleton, or inhibits spindle formation. Several of these latter types of agents are known to be chemotherapeutic agents. In yet another embodiment, the peptide is conjugated to another peptide such as one with binding specificity for EGFR, ErbB3, or ErbB4. In another embodiment, the composition comprises the peptide with a liposome or viral particle (e.g., for delivery in gene therapy).

The functional equivalents of EBP can be comprised of amino acids or peptidomimetics. In one embodiment, the functional equivalent is selected from the group consisting of a phage library member, a synthetic peptide library member, a combinatorial chemical library member, and a peptidomimetic.

The foregoing embodiments relating to the peptides and functional equivalents of the invention apply equally to all aspects of the invention.

In one embodiment, the composition further comprises a pharmaceutically acceptable carrier, and optionally, the peptide or functional equivalent thereof is present in an effective amount. In other embodiments, the composition further comprises another therapeutic agent including but not limited to an anti-cancer agent. The composition may be provided in a sustained release vehicle. In various embodiments of the invention, the ErB2 binding peptides bind the extracellular domain of ErbB2 and, importantly, also inhibit the phosphorylation of ErbB2 (e.g., at particular tyrosine or serine residues, as described herein).

The invention also provides for isolated nucleic acid molecules that code for ErbB2 binding peptides. Thus, in yet another aspect, an isolated nucleic acid molecule is provided comprising (a) a nucleic acid molecule which codes for a peptide comprising an amino acid sequence of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:33, SEQ ID NO:34, SEQ ID NO:35, SEQ ID NO:36, SEQ ID NO:37, SEQ ID NO:38 and SEQ ID NO:39 (i.e., SEQ ID NO:1 through to SEQ ID NO:13 inclusive and SEQ ID NO:33 through to SEQ ID NO:39 inclusive) or functionally equivalent fragments thereof, (b) degenerates of (a); and (c) complements of (a) and (b).

In some embodiments, the isolated nucleic acid molecule comprises a nucleotide sequence selected from the group consisting of SEQ ID NO:14 through to SEQ ID NO:26 and SEQ ID NO:40 through to SEQ ID NO:46, inclusive, and degenerates thereof. Using the nucleic acid codons provided herein, one of ordinary skill in the art will readily determine the nucleic acid sequences that are degenerates thereof. The invention similarly embraces these latter nucleic acid sequences.

The invention further provides in another aspect an expression vector comprising the afore-mentioned isolated nucleic acid molecule, preferably operably linked to a promoter, and host cells transformed or transfected with the expression vectors.

In another aspect, the invention provides a method for preventing or treating a disorder characterized by ErbB2 overexpression. The method can be used to prevent the disorder in a subject at risk of developing the disorder or, alternatively, to treat the disorder in a subject having the disorder. In embodiments of either, the methods further comprise first selecting a subject to be treated (e.g., a subject having the disorder or a subject at risk of developing the disorder).

In another aspect, a pharmaceutical preparation is provided comprising one or a combination of the afore-mentioned compositions and a pharmaceutically acceptable carrier. The pharmaceutical preparation and compositions may be in a sustained release vehicle.

The method comprises administering to a subject in need of such treatment an ErbB2 binding peptide that binds to an extracellular domain of ErbB2, and preferably inhibits phosphorylation of ErbB2. In some important embodiments, the ErbB2 binding peptide comprises an amino acid sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:33, SEQ ID NO:34, SEQ ID NO:35, SEQ ID NO:36, SEQ ID NO:37, SEQ ID NO:38 and SEQ ID NO:39, inclusive, or functional equivalents thereof. Functional equivalents thereof include fragments of the peptide that are capable of binding specifically to the extracellular domain of ErbB2. In some embodiments, the EBP or functional equivalent thereof is administered in an amount effective to inhibit the disorder. In other embodiments, the method involves co-administering an anti-cancer agent to the subject. In these latter embodiments, the peptide and the anti-cancer agent are co-administered in a combined effective amount to inhibit the disorder. In related aspects of the foregoing methods non-peptide small molecules that functionally and/or structurally mimic the EBP of the invention can also be used in place of the EBPs.

In one embodiment, the disorder is in or is likely to be in a tissue selected from the group consisting of the breast, ovary, uterus, cervix, thyroid gland, gastrointestinal tissue, colon, stomach, lung and bladder. In important embodiments, the disorder is a cancer. The cancer may be a primary tumor or a metastasis. The cancer may be selected from the group consisting of breast cancer, ovarian cancer (including endometrioid carcinoma), Ewing's sarcoma, cervical cancer, colorectal cancer (e.g., colorectal adenomas and adenocarcinomas), thyroid cancer, lung cancer, prostate cancer, stomach cancer, and bladder cancer.

In one embodiment, the peptide is administered systemically. In another embodiment, the peptide is administered locally. In yet another embodiment, the peptide is administered in a plurality of administrations. In another embodiment, the method further comprises administering to the subject an anti-cancer agent.

The invention further provides a method for inhibiting a metastasis (e.g., preventing tumor cell metastasis) by administering to a subject in need of such treatment one or a combination of any of the above-identified peptides or functional equivalents in an amount effective to prevent the formation or development of a metastasis. The metastasis may be present in bone marrow, lung, brain, and liver, but is not so limited.

In another aspect, the invention provides a method for detecting a cell characterized by ErbB2 overexpression comprising contacting an ErbB2 binding peptide, that in some embodiments comprises an amino acid sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:33, SEQ ID NO:34, SEQ ID NO:35, SEQ ID NO:36, SEQ ID NO:37, SEQ ID NO:38 and SEQ ID NO:39, or functional equivalent thereof, to a cell, and determining the level of binding of the peptide to the cell, wherein a level of binding greater than a control level is indicative of ErbB2 overexpression by the cell.

In one embodiment, the contacting occurs in vivo and the peptide is administered to a subject. In a related embodiments, the peptide may be administered systemically or locally. In important embodiments, the peptide is conjugated to a detectable label. The detectable label may be selected from the group consisting of a radioisotope, a contrast agent, and a gaseous agent, but is not so limited.

In one embodiment, the cell is a breast tissue cell. In another embodiment, the cell is present in a population selected from the group consisting of bone marrow cells, lung cells, brain cells, and liver cells. In a related embodiment, the cell is harvested from a subject having a disorder characterized by ErbB2 overexpression, prior to treating the subject with radiation or chemotherapy. The disorder characterized by ErbB2 overexpression may be breast cancer, but is not so limited.

In one embodiment, the method further comprises removing the cell characterized by ErbB2 overexpression from a tissue or cell population in which it exists. In one embodiment, the cell is removed from the tissue or cell population using flow cytometry. In some embodiments, solid matrix (e.g., agarose beads or magnetic particles) affinity methods are used in combination with the peptides or functional equivalents thereof. In another embodiment, the cell is removed from the tissue or cell population using a cytotoxic agent. The cytotoxic agent may be conjugated to the peptide, or functional equivalent thereof.

In another aspect, a method is provided for identifying a compound that binds to ErbB2 and inhibits interaction between ErbB2 and an ErbB2 binding peptide (that preferably comprises an amino acid sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:33, SEQ ID NO:34, SEQ ID NO:35, SEQ ID NO:36, SEQ ID NO:37, SEQ ID NO:38 and SEQ ID NO:39, or functional equivalent thereof). The method comprises (1) performing a first assay between ErbB2 and the peptide or functional equivalent thereof to obtain a first assay result; (2) performing a second assay between ErbB2 and the peptide or functional equivalent thereof in the presence of a compound to obtain a second assay result; and (3) comparing the first and second assay results to determine whether the compound inhibits interaction between ErbB2 and the peptide or functional equivalent thereof. In some important embodiments, the ErbB2 molecule is the extracellular domain of ErbB2. The method may also include a negative pre-screen in which compounds are initially tested and negatively selected based on their ability to bind to other ErbB family members.

In one embodiment, the compound is a molecular library member. The molecular library may be selected from the group consisting of a peptide library such as a phage display peptide library, a peptidomimetic library, a combinatorial chemistry library, a synthetic peptide library, and a natural compound library. The screening method may further comprise selecting a molecular library that is suspected of containing a library member that modulates the interaction of ErbB2 and an ErbB2 ligand. The molecular library may contain from two to $10^{15}$ molecules and any integer number therebetween. In an important embodiment, the compound is a phage display library member. The phage display library member may be cyclized.

In one embodiment, the assay is a binding assay which detects binding of ErbB2 to the peptide or functional equivalent thereof. In another embodiment, the assay is a signaling assay which detects signaling events following ErbB2 binding to the EBP. In yet a further embodiment, the method further involves introducing the molecular library member, and in some instances conjugates of a library member with a therapeutic agent, into an animal model of a condition characterized by overexpression of ErbB2 and determining whether the molecular library member ameliorates symptoms of the condition.

In one embodiment, the peptide may be cyclized. In another embodiment, ErbB2 or the peptide or functional equivalent thereof may be immobilized onto a solid support such as for example an agarose bead or a magnetic particle. According to one embodiment, ErbB2 is present in the context of a cell. The cell may be selected from the group consisting of breast cancer cell and an ovarian cancer cell.

These and other aspects of the invention will be described in greater detail herein.

Each of the aspects of the invention can encompass various embodiments of the invention. It is therefore anticipated that each of the embodiments of the invention involving any one element or combinations of elements can be included in each aspect of the invention.

BRIEF DESCRIPTION OF THE SEQUENCE LISTING

SEQ ID NO:1 is the amino acid sequence of ErbB2-binding peptide 1 (EBP-1; EC-1).

SEQ ID NO:2 is the amino acid sequence of ErbB2-binding peptide 2 (EBP-2).

SEQ ID NO:3 is the amino acid sequence of ErbB2-binding peptide 3 (EBP-3).

SEQ ID NO:4 is the amino acid sequence of ErbB2-binding peptide 4 (EBP-4).

SEQ ID NO:5 is the amino acid sequence of ErbB2-binding peptide 5 (EBP-5).

SEQ ID NO:6 is the amino acid sequence of ErbB2-binding peptide 6 (EBP-6).

SEQ ID NO:7 is the amino acid sequence of ErbB2-binding peptide 7 (EBP-7).

SEQ ID NO:8 is the amino acid sequence of ErbB2-binding peptide 8 (EBP-8).

SEQ ID NO:9 is the amino acid sequence of ErbB2-binding peptide 9 (EBP-9).

SEQ ID NO:10 is the amino acid sequence of ErbB2-binding peptide 10 (EBP-10).

SEQ ID NO:11 is the amino acid sequence of ErbB2-binding peptide 11 (EBP-11).

SEQ ID NO:12 is the amino acid sequence of ErbB2-binding peptide 12 (EBP-12).

SEQ ID NO:13 is the amino acid sequence of ErbB2-binding peptide 13 (EBP-13).

SEQ ID NO:14 is a putative nucleic acid sequence coding for EBP-1.

SEQ ID NO:15 is a putative nucleic acid sequence coding for EBP-2.

SEQ ID NO:16 is a putative nucleic acid sequence coding for EBP-3.

SEQ ID NO:17 is a putative nucleic acid sequence coding for EBP-4.

SEQ ID NO:18 is a putative nucleic acid sequence coding for EBP-5.

SEQ ID NO:19 is a putative nucleic acid sequence coding for EBP-6.

SEQ ID NO:20 is a putative nucleic acid sequence coding for EBP-7.

SEQ ID NO:21 is a putative nucleic acid sequence coding for EBP-8.

SEQ ID NO:22 is a putative nucleic acid sequence coding for EBP-9.

SEQ ID NO:23 is a putative nucleic acid sequence coding for EBP-10.

SEQ ID NO:24 is a putative nucleic acid sequence coding for EBP-11.

SEQ ID NO:25 is a putative nucleic acid sequence coding for EBP-12.

SEQ ID NO:26 is a putative nucleic acid sequence coding for EBP-13.

SEQ ID NO:27 is the nucleic acid sequence of ErbB2 mRNA (GenBank Accession Number M11730). See Appendix A for the GenBank submission.

SEQ ID NO:28 is the amino acid sequence of ErbB2 protein (GenBank Accession Number M11730). See Appendix A for the GenBank submission.

SEQ ID NO:29 is the amino acid sequence of a biased peptide phage library.

SEQ ID NO:30 is the amino acid sequence of a biased peptide phage library.

SEQ ID NO:31 is the amino acid sequence of a biased peptide phage library.

SEQ ID NO:32 is the amino acid sequence of a biased peptide phage library.

SEQ ID NO:33 is the amino acid sequence of ErbB2-binding peptide 14 (EBP-14; 02–124) derived from a biased peptide phage library.

SEQ ID NO:34 is the amino acid sequence of ErbB2-binding peptide 15 (EBP-15; 02–137) derived from a biased peptide phage library.

SEQ ID NO:35 is the amino acid sequence of ErbB2-binding peptide 16 (EBP-16; 02–140) derived from a biased peptide phage library.

SEQ ID NO:36 is the amino acid sequence of ErbB2-binding peptide 17 (EBP-17; 02–135) derived from a biased peptide phage library.

SEQ ID NO:37 is the amino acid sequence of ErbB2-binding peptide 18 (EBP-18; E-20) derived from a random peptide phage library.

SEQ ID NO:38 is the amino acid sequence of ErbB2-binding peptide 19 (EBP-19; C-19) derived from a random peptide phage library.

SEQ ID NO:39 is the amino acid sequence of ErbB2-binding peptide 20 (EBP-20; C-25) derived from a random peptide phage library.

SEQ ID NO:40 is a putative nucleic acid sequence coding for EBP-14.

SEQ ID NO:41 is a putative nucleic acid sequence coding for EBP-15.

SEQ ID NO:42 is a putative nucleic acid sequence coding for EBP-16.

SEQ ID NO:43 is a putative nucleic acid sequence coding for EBP-17.

SEQ ID NO:44 is a putative nucleic acid sequence coding for EBP-18.

SEQ ID NO:45 is a putative nucleic acid sequence coding for EBP-19.

SEQ ID NO:46 is a putative nucleic acid sequence coding for EBP-20.

BRIEF DESCRIPTION OF THE FIGURES

FIG. 1A is a bar graph showing ELISA results using the E12 and CB1 peptide phage clones.

Figure 1B:
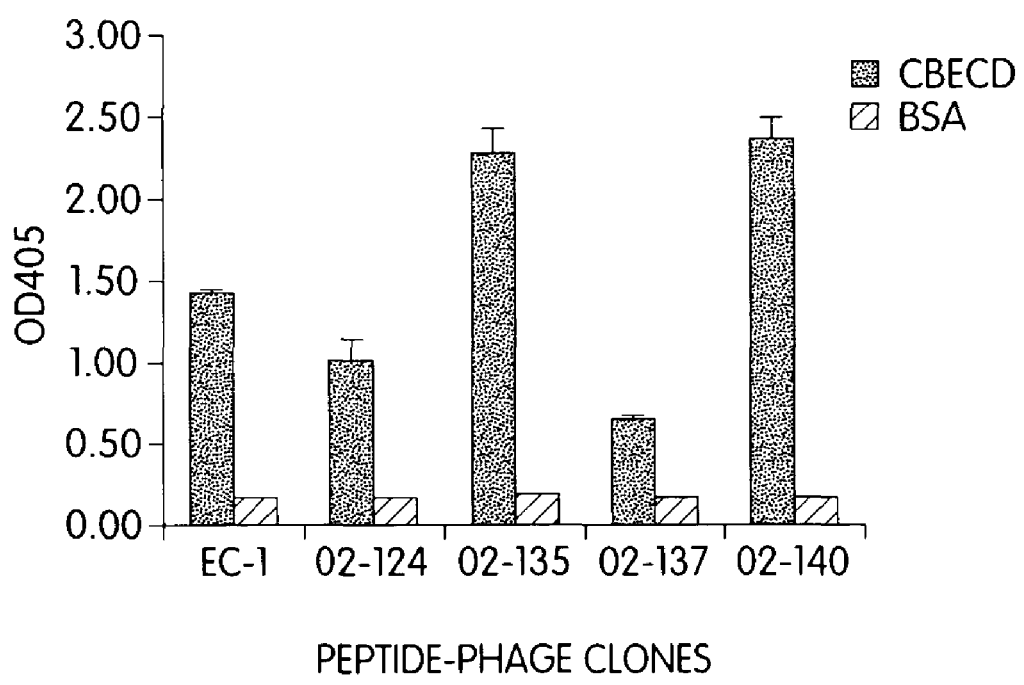
FIG. 1B is a bar graph showing ELISA results using EC-1 and new clones isolated from EC-1 biased phage display libraries. The graph shows binding to the extracellular domain of ErbB2 (CBECD) and the control binding to BSA.

It is to be understood that the drawings are not required for enablement of the claimed invention.

DETAILED DESCRIPTION OF THE INVENTION

The invention relates in part to the identification and use of peptides that bind specifically to ErbB2, and more specifically to the extracellular domain of ErbB2. These peptides are referred to herein as ErbB2 binding peptides (i.e., EBP). In addition to binding ErbB2, the EBP can also interfere with the functioning of ErbB2 (particularly in cancer cells) by interfering with the ability of ErbB2 to become phosphorylated, to interact with other compounds (e.g., polypeptides such as ErbB1 (EGFR), ErbB3, ErbB4 or mucins such as mucin 4), and/or to transduce a signal into a cell. The peptides, and their functional equivalents are useful in the diagnosis and treatment of disorders characterized by ErbB2 overexpression. They are also useful in the isolation and, optionally, removal of cells that overexpress ErbB2 (e.g., tumor cells). These peptides can also be used to identify further EBP. These and other aspects will be described in greater detail herein.

ErbB2 is the human homolog of the protein encoded by the neu oncogene and is a receptor-like tyrosine kinase. As used herein, ErbB2 is referred to as HER-2 and c-neu protein interchangeably. The nucleotide and amino acid sequence of the human c-erbB2 mRNA and ErbB2 protein are provided herein as SEQ ID NO:27 and SEQ ID NO:28 (from GenBank Accession Number X03363). ErbB2 mRNA is approximately 4.8 kb in length and the protein it encodes is 1255 amino acids in length and approximately 185 kilodalton (kD). ErbB2 has an extracellular domain having two cysteine rich repeat clusters, a transmembrane domain, and an intracellular kinase domain. The polypeptide can be glycosylated at a number of sites. The extracellular domain corresponds to nucleotides 151 to 2109 relative to SEQ ID NO:27 and amino acid residues 1 to 653 relative to SEQ ID NO:28 (GenBank Accession Number M11730). (Coussens et al., Science 230:1132.)

ErbB2 is expressed at low or negligible levels in most normal adult tissues, with the possible exception of kidney. (Mori et al., Laboratory Investigation, 61:93.) ErbB2 is expressed fetal tissues including fetal renal tubules and fetal epithelium. (Natali et al., Int. J. Cancer, 1990 45(3):457–461.) ErbB2 gene amplification has been observed in a number of primary cancers, metastatic lesions, and cancer cell lines. This amplification results in ErbB2 overexpression in several tumor types including breast carcinoma, glioblastoma, lung cancer, prostate cancer, salivary gland adenocarcinoma, gastric and colon adenocarcinomas, renal adenocarcinoma, mammary gland carcinoma, ovarian cancer, cervical cancer, colorectal carcinomas and adenocarcinomas, thyroid tumors, Ewing's sarcoma, and squamous carcinomas. Moreover, ErbB2 overexpression is found in tumors of 30% of breast cancer patients and this increase in expression correlates with poor patient prognosis. In several breast cancer cell lines, ErbB2 is co-amplified with Grb7 by virtue of the fact that erbB2 and the gene that codes for Grb7 are located close to each other on chromosome 17. Combined overexpression of ErbB2 and Grb7 proteins in these tumors likely up-regulates a signaling pathway which plays an important role in tumor pathogenesis. (Janes et al., 1997, J Biol Chem 272: 8490–8497; Tanaka et al., 1997 Cancer Research 57:28–31.) ErbB2 overexpression has also been reported to be associated with early stages of colorectal cancer, as it has been demonstrated that pre-neoplastic lesions express higher levels of ErbB2 than do neoplastic lesions.

The invention involves, in various related and interconnected aspects, isolated ErbB2-binding peptides (i.e., EBP), functional equivalents and modifications and variants thereof, unique fragments thereof, nucleic acid molecules encoding the foregoing, as well as diagnostics and therapeutics relating thereto.

The invention provides in one aspect peptides comprising an amino acid sequence selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:33, SEQ ID NO:34, SEQ ID NO:35, SEQ ID NO:36, SEQ ID NO:37, SEQ ID NO:38 and SEQ ID NO:39, and functional equivalents thereof. The amino acid sequences of the EBP of the invention (EBP-1 through to EBP-20, respectively) are listed in Table 1.

TABLE 1

| Peptide SEQ ID NO: | Amino Acid Sequence |
|---|---|
| SEQ ID NO:1 | WTGW C LNPEESTWGF C TGSF |
| SEQ ID NO:2 | VVA C SWDWTMGAVV C YERI |
| SEQ ID NO:3 | GFWT C EYDWWSDATV C MHTL |
| SEQ ID NO:4 | GRGW C WSEWQNDWFW C WDVW |
| SEQ ID NO:6 | ARLQ C WSLGWGGPVY C GFGQ |
| SEQ ID NO:7 | IQEV C WFDYNLSQWH C MTVI |
| SEQ ID NO:8 | PDIY C LSVTAPGFLI C YERY |
| SEQ ID NO:9 | HDEL C VFSFDFNALL C WPAE |
| SEQ ID NO:10 | LNWE C WYDYRLEAWD C RGDI |
| SEQ ID NO:11 | C EVWGEVPWT C |
| SEQ ID NO:12 | C EVWGFVPWA C |
| SEQ ID NO:13 | SNES C GSPINPWGEM C LLML |
| SEQ ID NO:33 | WTGW C LNPEESTWGF C RSAG |
| SEQ ID NO:34 | WTGW C LSPEESTWGF C RSAG |
| SEQ ID NO:35 | WTGW C LNPEESTWGF C SGYI |
| SEQ ID NO:36 | WTGW C FDDNHSTWGF C TGSF |
| SEQ ID NO:37 | DTDM C WWWSREFGWE C AGAG |
| SEQ ID NO:38 | SLAL C LSEGVLLGAD C RVLF |
| SEQ ID NO:39 | WSSM C GDPTIADWLW C FSDA |

The peptides can exhibit therapeutic activity by binding to and inhibiting the activity of ErbB2. Such an activity is not dependent upon conjugation of the peptide to a cytotoxic agent. Accordingly, in one aspect, the EBP are ErbB2 antagonists. In this sense, the peptides may block the interaction of ErbB2 with its native ligand(s) or with other proteins with which ErbB2 interacts such as other ErbB family members (e.g., ErbB1, ErbB3 or ErbB4). The ability to block the interaction of ErbB2 (either in monomeric or dimeric form) with ErbB1, ErbB3 or ErbB4 may be particularly important for inhibiting metastatic spread in a subject. Accordingly, peptides capable of inhibiting such interactions are particularly suitable to the prevention or treatment of metastasis. The peptides of the invention can also function by inhibiting the formation of larger complexes that contain ErbB2. In this latter instance, the peptides bind directly to ErbB2 yet their effect is indirect in that they preclude ErbB2 interacting proteins (such as ErbB1, ErbB3 and ErbB4) from interacting with other peptides or polypeptides (such as, for example, heregulin).

To date, few native ErbB2 ligands have been identified. One such ligand is the membrane mucin MUC4/sialomucin (SMC) complex which reportedly contacts ErbB2 via an intramembrane domain. As a result, both ErbB2 and SMC are expressed by the same cell in order for interaction to occur. Binding of SMC by ErbB2 reportedly modulates the phosphorylation status of ErbB2 in the presence and absence of heregulin. It has been reported that expression of SMC promotes tumor growth in vivo. The peptides of the invention can be used to preclude the binding of ErbB2 to SMC or to disrupt pre-formed complexes between ErbB2 and SMC.

Heterodimers of ErbB2 with ErbB1, ErbB3 or ErbB4 appear to evade normal cellular controls by, for example, decreasing the rate of internalization or avoiding degradation once internalized. It has been postulated that one way in which ErbB2 functions in cancers is to avoid internalization, leading to continuous cell surface expression of an activated receptor tyrosine kinase. The peptides of the invention can be used to induce overall cellular ErbB2 internalization by, for example, increasing internalization rates. One way in which the peptides can accomplish this is by conjugation to internalization sequences such as translocation sequences. The peptides of the invention can also prolong the internalization time of ErbB2, for example, by increasing the time necessary to degrade the peptide/ErbB2 complex and/or stimulating degradation of ErbB2 once it is internalized. Interference with the normal trafficking of internalized ErbB2can lead to lower levels of ErbB2 on the cell surface.

It is clear that ErbB2 overexpression is a hallmark of many cancer types, and particularly a hallmark of metastatic cells in such cancers. Thus, ErbB2 may be involved in the homing of primary cancer cells to secondary sites within the body. The peptides of the invention by binding to the extracellular domain of ErbB2 may block ErbB2 interactions necessary for malignant and metastatic phenotypes.

The peptides may also impact upon signaling events downstream of ErbB2 extracellular engagement. As an example, ErbB2 may signal intracellularly during interaction with its native ligand or other factors with which it dimerizes or complexes. Such signaling may determine the malignant and metastatic phenotype of the ErbB2 expressing cell. The peptide may prevent this by blocking such interaction yet not mimicking the signal transduction induced by the native ligand. ErbB2 containing heterodimers can recruit MAPK and P13K. Signaling through ErbB2 reportedly affects activation of cyclin and CDK complexes, thereby inhibiting apoptosis and stimulating proliferation of such cells. Downstream targets of ErbB2 signaling include cell cycle regulators such as $p21^{waf1}$.

EBPs and functional equivalents thereof which function as ErbB2 antagonists can be used in combination with other therapeutic agents in order to inhibit a disorder characterized by ErbB2 overexpression. It is expected that such a combination will yield a synergistic response (i.e., one that is greater than the additive effects of the therapeutic agents when used alone) because the EBP and the other therapeutic agents will generally function via different pathways.

Accordingly, the combination can be used to increase the efficacy of a particular therapeutic agent without the need for higher doses (and associated systemic toxicity) of the therapeutic agent.

Another synergistic combination is the administration of the peptides of the invention with an anti-estrogen. It has been reported that estrogen can modulate ErbB2 signaling via the estrogen receptor. Accordingly, the combination of an EBP with an anti-estrogen can induce a synergistic response.

The peptides bind strongly and specifically to the extracellular domain of ErbB2. As shown in the Examples, peptide phage displaying a peptide having an amino acid sequence of SEQ ID NO:1 through to SEQ ID NO:13, and SEQ ID NO:33 through to SEQ ID NO:39, inclusive, yield a reproducible ErbB2-specific signal by ELISA and immunofluorescence assay. By binding to the extracellular domain of ErbB2, the EBP can inhibit the function of ErbB2 by, at a minimum, preventing its association with extracellular factors such as its naturally occurring ligand(s). Specific inhibitors of ErbB2 are useful in elucidating the complete function and exact role of ErbB2 in cancer progression, as well as in the development of cancer therapeutics which target ErbB2. The peptides bind specifically to ErbB2 and not to any other member of the ErbB family of growth factor receptors. In some embodiments, the peptides bind with greater affinity to ErbB2 than to other proteins (e.g., more than a five fold greater affinity, more than a ten fold greater affinity or more than a fifty fold greater affinity).

Other peptides and polypeptides that bind to ErbB2 have been identified previously, including Herceptin, a monoclonal antibody specific for ErbB2 (Genentech, Inc., South San Francisco, Calif.). Due to their small size, the peptides of the invention can have improved pharmacokinetics, including increased tumor targeting and penetration. Park et al. recently reported the identification of another peptide that binds to the extracellular domain of ErbB2. (Park et al., Nature Biotechnology, 18:194.) The peptide inhibited in vitro cell proliferation and colony formation, as well as in vivo tumor formation in nude mice bearing ErbB2-overexpressing cells. It also increased the sensitivity of ErbB2-overexpressing cells to radiation and significantly increased the effectiveness of doxorubicin inhibition of tumor growth when administered concurrently. Park et al. rationally designed the peptide based on the structure of CDR regions from a known anti-ErbB2 antibody. The peptides of the present invention share no homology with that reported by Park et al.

As described in the Examples, the EBP of the invention were generated and identified using random peptide phage display technology. Using this technology, it was possible to produce and screen candidate peptides more rapidly and with less cost than would have been possible with for example antibody technology. Accordingly, the discovery of the lead compounds described herein was significantly faster and less expensive than traditional methods of lead discovery.

As indicated in Table 1, all the EBP possess at least two cysteine residues between which there exists a stretch of 9–10 amino acid residues. Additionally, the EBP may also possess flanking amino acid sequences beyond the cysteines at either or both their amino or carboxy ends. The length of the EBP ranges from 11–20 amino acid residues.

Although listed above in linear form, the EBP may be cyclic as well, or at least capable of being cyclized. One way in which the EBP may be easily cyclized is through the formation of a disulfide bond between the two cysteines commonly possessed by each of the EBP. Alternatively, one or more cysteine residues may be introduced into the peptides. As indicated by the EBPs of Table 1, it is not necessary that the cysteine residues be located at the ends of the peptides (i.e., at the first and last amino acid positions). Rather, it is only required that the cysteine residues are spaced far enough apart from each other to allow for a disulfide bond to be formed (e.g., with 4, 5, 6, 7, 8, 9, 10, 11, 12, 13, 14, 15, 16, 17, 18, 19, 20 or more residues in between the two cysteine residues). The peptide having an amino acid sequence of SEQ ID NO:1 is an example of a peptide in which the disulfide bonded cysteines may be those already present at positions 5 and 16, or alternatively, additional cysteine residues may be added to the amino and carboxy termini. In some instances, it may be preferable to substitute thio-ether linkages for the disulfide bond produced between cysteine residues. Such a modification is described in PCT patent application WO 98/02176 (PCT/US97/12501), and in Oligino et al., 1997, J Mol Chem 272:29046–29052 and Lou et al., 1999, Arch Biochem Biophys, 372:309–314.

In still other embodiments, the linkage may be a peptide linkage between the two arms of the peptide. It is to be understood that the invention embraces other varieties of linkages known in the art for the purpose of producing a cyclic peptide. The proceeding examples of linking molecules are also suitable for the conjugation of EBP to agents such as diagnostic (e.g., imaging agents) and therapeutic (e.g., anti-cancer) agents. Examples of suitable linking molecules which can be used include bifunctional crosslinker molecules. The crosslinker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available crosslinkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bis-maleimidohexane, 1,4-di-[3'-(2'-pyridyldithio)-propionamido)]butane, 1-[p-azidosalicylamido]-4-[iodoacetamido] butane, and N-[4-(p-azidosalicylamido) butyl]-3'-[2'-pyridyldithio]propionamide. Crosslinkers preferentially reactive with carbohydrates include azidobenzoyl hydrazine. Crosslinkers preferentially reactive with carboxyl groups include 4-[p-azidosalicylamido]butylamine. Heterobifunctional cross-linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[3-dimethylaminopropyl]carbodiimide hydrochloride. Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio]propionyl hydrazide. The cross-linkers are bis-

[β-4-azidosalicylamido)ethyl]disulfide and glutaraldehyde. Amine or thiol groups may be added at any nucleotide of a synthetic nucleic acid so as to provide a point of attachment for a bifunctional crosslinker molecule. The nucleic acid may be synthesized incorporating conjugation-competent reagents such as Uni-Link AminoModifier, 3'-DMT-C6-Amine-ON CPG, AminoModifier II, N-TFA-C6-Amino-Modifier, C6-ThiolModifier, C6-Disulfide Phosphoramidite and C6-Disulfide CPG (Clontech, Palo Alto, Calif.). The peptides of the invention can also comprise one or more non-peptide linkages in their backbones.

The invention further intends the use of fragments of the EBPs disclosed herein, including unique fragments and functionally equivalent fragments of the EBPs in the diagnostic and therapeutic methods described herein. Unique fragments can be used to prepare antibodies that are specific for the EBP. Functionally equivalent fragments are useful as substitutes for the EBPs of the invention. This is particularly useful when achieving the smallest ErbB2-binding peptide possible is desired.

A unique fragment of an EBP, in general, has the features and characteristics of unique fragments of nucleic acid molecules as discussed herein. A unique fragment can act as a signature for identifying peptides or polypeptides that comprise the amino acid sequences selected from the group consisting of SEQ ID NO:1 through to SEQ ID NO:13, and SEQ ID NO:33 through to SEQ ID NO:39, inclusive. Such polypeptides may be native binding partners of ErbB2, and more preferably, may be native inhibitory binding partners of ErbB2. Those skilled in the art are well versed in methods for selecting unique amino acid sequences. A comparison of the sequence of the fragment to those in known databases is all that is typically required. Preferably, the unique fragment is unique in humans, i.e., it is long enough to assure that its precise sequence is not found in other molecules encoded by the human genome which have been identified and publicly disclosed as of the date of invention and/or the filing date of this application.

As will be recognized by those skilled in the art, the size of the unique fragment will depend upon factors such as whether the fragment constitutes a portion of a conserved motif. Thus, some regions of SEQ ID NO:1 will require longer segments to be unique while others will require only short segments, typically between 5 and 12 amino acids (e.g., 5, 6, 7, 8, 9, 10, 11 and 12 amino acids long or more, including each integer up to the full length). Virtually any segment of SEQ ID NO:1 through to SEQ ID NO:13, and SEQ ID NO:33 through to SEQ ID NO:39, inclusive, that is 9 or more amino acids in length will be unique.

Unique fragments preferably will have the same functionality as the full length peptides provided herein, including the ability to bind to the extracellular domain of ErbB2. The unique fragments can be used in place of the full length peptides in order to inhibit or interfere with ErbB2 functioning (e.g., binding to another compound or signal transduction), or they can be used to generate binding partners to the full length peptide (e.g., antibodies). Unique fragments may be those that 1, 2, 3, 4, 5, 6, 7, 8, 9, 10, 11, 12, 13, 14, 15, 16, or 17 amino acids of the full length peptide. In preferred embodiments, the unique fragments are at least 5, at least 10, or at least 15 amino acids in length.

One particularly important subset of EBP fragments are functionally equivalent fragments of EBP. Generally, a "functional equivalent of an EBP" is a peptide or small molecule that is able to function in a similar manner to an EBP disclosed herein. For example, the functional equivalent would bind to ErbB2 and interfere with the functioning of ErbB2 and its role in tumorigenesis and metastasis. The functional equivalent may be capable of inhibiting ErbB2 interaction with other factors and/or disrupting pre-formed complexes that contain ErbB2. The ability of a functional equivalent to bind to ErbB2 specifically can be determined using the binding assays described herein or known in the art. The preferred functional equivalents are those that bind specifically to the extracellular domain of ErbB2 but not to other ErbB family members. The functional equivalent of the EBP may be peptide, non-peptide or chimeric in nature. The synthesis of such functionally equivalent variants is described below. In some preferred instances, a functional equivalent mimics the EBP of the invention with respect to size, structure, and charge distribution. In other embodiments, the functional equivalent mimics the EBP of the invention by comprising partial sequence from the EBPs described herein. For example, a functional equivalent can be a peptide that is identical to an EBP described herein at, for example, 10%, 20%, 30%, 40%, 50%, 60%, 70%, 80%, 90% or 95% of the amino acid positions, with the non-identical positions occupied by conservative amino acids or amino acid analogs. In some embodiments, non-conservative amino acid substitutions can also be introduced into the functional equivalents. Accordingly, functional equivalents of 11 amino acid peptides may have 1, 2, 3, 4, 5, 6, 7, 8, 9, 10 or 11 substitutions, while those functional equivalents of 19 or 20 amino acid peptides may have 1, 2, 3, 4, 5, 6, 7, 8, 9, 10, 11, 12, 13, 14, 15, 16, 17, 18, 19 or 20 substitutions. Preferably, the functional equivalent peptides have substitutions at fewer than 50% of the amino acid positions, at fewer than 40% of the amino acid positions, at fewer than 30% of the amino acid positions, at fewer than 20% of the amino acid positions, or at fewer than 10% of the amino acid positions.

In other embodiments, functional equivalents of the peptides described herein possess a number of amino acids identical in sequence to the EBPs and such amino acids are arranged in a contiguous manner. That is, some functional equivalents possess 2, 3, 4, 5, 6, 7, 8, 9, 10, 11, 12, 13, 14, 15, 16, 17, or 18, or 19 contiguous amino acids that are identical in sequence to the EBPs described herein.

Functional equivalence refers to an equivalent activity (e.g., binding to ErbB2), however it also embraces variation in the level of such activity. For example, a functional equivalent is a variant that binds to ErbB2 with lesser, equal, or greater affinity than the EBPs described herein, provided that the variant is still useful in the invention (e.g., it binds specifically and uniquely to ErbB2, and optionally interferes with ErbB2 function).

The skilled artisan will realize that conservative amino acid substitutions may also be made in the EBP disclosed herein to provide functional equivalents of the foregoing peptides. As used herein, a "conservative amino acid substitution" refers to an amino acid substitution which does not alter the relative charge or size characteristics of the peptide or protein in which the amino acid substitution is made. Functional equivalents can be prepared according to methods for altering peptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functional equivalents of the EBPs include conservative amino acid substitutions of SEQ ID NO:1 through to SEQ ID NO:13, inclusive. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of EBPs to produce functionally equivalent variants may be made by alteration of nucleic acid molecules encoding the EBPs (e.g., SEQ ID NO:14 through to SEQ ID NO:26, and SEQ ID NO:40 through to SEQ ID NO:46, inclusive, and degenerates thereof). Such substitutions can be made by a variety of methods known to one of ordinary skill in the art. For example, amino acid substitutions may be made by chemical synthesis of a nucleic acid molecule encoding an EBP using an automated DNA synthesizer, for example. The activity of functionally equivalent fragments of the EBP can be tested by cloning the nucleic acid molecule encoding the altered EBP into a bacterial or mammalian expression vector, introducing the vector into an appropriate host cell, expressing the altered EBP, and testing for the functional capability of the EBPs so produced using methods as disclosed herein.

In some preferred embodiments, the peptides and functional equivalents thereof are prepared using chemical synthesis using standard peptide chemistry synthesis methods, with which the ordinary artisan will be familiar.

Modifications made to the nucleic acid molecules which encode EBPs can include deletions, point mutations, truncations, potentially resulting in amino acid additions, deletions or substitutions and can serve to: 1) enhance a property of an EBP, such as peptide stability in an expression system or the stability of peptide-protein binding; 2) provide a novel activity or property to an EBP, such as addition of an antigenic epitope, a detectable moiety or a localization signal sequence (such as the translocation sequences discussed herein); or 3) to provide equivalent or better binding to ErbB2. Alternatively, modifications can be made directly to the peptide, such as by cleavage, amino acid additions, deletions or substitutions including substitutions with non-natural amino acids, formation during peptide or peptidomimetic synthesis of bonds other than peptide bonds such as pseudo peptide bonds, addition of a linker molecule, addition of a detectable moiety, such as biotin, addition of a fatty acid, and the like. Modifications also embrace fusion proteins comprising all or part of the EBP amino acid sequence (i.e., SEQ ID NO:1 through to SEQ ID NO:13, and SEQ ID NO:33 through to SEQ ID NO:39, inclusive).

Mutations of nucleic acid molecules which encode EBPs preferably preserve the amino acid reading frame of the coding sequence, and preferably do not create regions in the nucleic acid molecule which are likely to hybridize to form secondary structures, such a hairpins or loops, which can be deleterious to expression of the variant peptide.

Mutations can be made by selecting an amino acid substitution, or by random mutagenesis of a selected site in a nucleic acid molecule which encodes the peptide. Variant peptides are then expressed and tested for one or more activities to determine which mutation provides a variant peptide with the desired properties. Further mutations can be made to EBPs and variants thereof that are silent as to the amino acid sequence of the peptide, but which provide preferred codons for translation in a particular host. The preferred codons for translation of a nucleic acid molecule in, e.g., E. coli, are well known to those of ordinary skill in the art. Still other mutations can be made to the noncoding sequences of nucleic acid molecules to enhance expression of the peptide.

The invention also embraces variants of the EBPs described above. As used herein, a "variant" of an EBP is a peptide or peptidomimetic which contains one or more modifications to the primary amino acid sequence of an EBP. The invention embraces variants of EBP that possess substituents at various positions. Modifications to the EBPs that preserve the size, structure, and charge distribution of the EBP are preferred in some embodiments. A person of ordinary skill in the art is capable of determining the size, structure, and charge distribution characteristics of the EBPs disclosed herein and of designing other putative inhibitory agents based on this knowledge.

Variants can include peptides which are modified specifically to alter a feature of the polypeptide unrelated to its binding and inhibitory activity. For example, cysteine residues can be substituted or deleted to prevent disulfide linkages, which may be desirable if other means of linkage are available in the peptide. Similarly, certain amino acids can be changed to enhance expression of the variant by eliminating proteolysis by proteases in an expression system (e.g., dibasic amino acid residues in yeast expression systems in which KEX2 protease activity is present).

It will be apparent to one of ordinary skill in the art that the invention embraces the synthesis of a wide variety of variants having any combination of amino acid analogs and/or peptidomimetic residues as described above and as are known in the art. (See, for example, Burke, et al., Bio. Med. Chem. Lett., 9:347–352, 1999.) Non-amino acid substitutions are known in the art and are described in, inter alia, Burke et al., 1999, Bioorg Med Chem Lett, 25 9:347–352; Long et al., 1999, Biochem Biophys Res Commun 264: 902–908; Yao et al., 1999, J. Med Chem, 42:25–35; Ye et al., 1995, J Med Chem, 38:4270–4275. Glutamine (Glu) residues may be replaced with α-amino-adipate (Adi) molecules and tyrosine positions may be substituted with 4-carboxymethyl-Phe. Glutamic acid residues can be modified to possess an additional methylene group or they may simply be substituted with α-amino-adipate. Such modifications have been found to increase binding affinity in some species of antagonists. (Long et al., 1999, Biochem. Biophys. Res. Commun. 264:902–908.) Yao et al. reported the synthesis and use of N-α-oxalyl groups in certain signaling inhibitory molecules. (Yao, et al., J. Med. Chem., 42:25–35, 1999) Other residues which may be incorporated into the ErbB2 specific variants include the non-naturally occurring amino acid 1-aminocyclohexylcarboxylic acid ($Ac_6c$) or 1-aminocyclohexanecarboxylic acid as replacements for glutamic acid residues. (Gay et al., Int. J. Cancer, 83:235–241, 1999). Other non-naturally occurring amino acids can be used such as 2-azetidinecarboxylic acid or pipecolic acid (which have 6-membered, and 4-membered ring structures respectively) for proline residues, and S-ethylisothiourea, 2-$NH_2$-thiazoline and 2-$NH_2$-thiazole. Also useful in the synthesis of EBP variants is the use of an asparagine residue substituted with 3-indolyl-propyl at the C terminal carboxyl group. Further potential modifications of EBPs envisioned by the invention include modifications of cysteines, histidines, lysines, arginines, tyrosines, glutamines, asparagines, prolines, and carboxyl groups as are well known in the art and are described in U.S. Pat. No. 6,037,134. Synthesis of the afore-mentioned variants is described in the cited references and is well within the realm of one of ordinary skill in the art.

The EBP may be modified to introduce or stabilize certain structural features. As an example, structural features including, but not limited to, β-turns can be introduced into inhibitory peptides. β-turns can be introduced into the EBP variants by synthesizing such variants with a proline residue or a glycine-proline combination, or a 1-aminocyclohexanecarboxylic acid as a substitution for glutamic acid residues.

(Garcia-Echeverria, J Med Chem. 41(11):1741–4, 1998) In other embodiments and as discussed above, it may be preferred that the variants possess a stable cyclic structure. This may be achieved by generating thio-ether cyclized peptides such as those reported by Oligino et al. and Lou et al. (Oligino et al., J. Biol. Chem. 272:29046–29052, 1997; Lou et al., Arch Biochem Biophys, 372:309–314, 1999) This modification ensures a stable conformation which, in some instances, may be optimal for ErbB2 binding and potentially functional inhibition. The cyclic structure can also be formed via other linkages such as, but not limited to, peptide bonds.

As used herein with respect to polypeptides, the term "isolated" means separated from its native environment in sufficiently pure form so that it can be manipulated or used for any one of the purposes of the invention. Thus, "isolated" means sufficiently pure to be used (i) to raise and/or isolate antibodies, (ii) as a reagent in an assay, (iii) as a therapeutic agent, or (iv) for sequencing, etc.

The EBP can be produced in a number of ways. In a preferred embodiment, the peptides are identified using a phage display technology as described in the Examples and in PCT patent application WO98/02176 (PCT/US97/12501). Alternatively, they may be synthesized using a peptide synthesizer. Alternatively, an expression vector which incorporates a nucleic acid molecule encoding the peptide, such as SEQ ID NO:14 through to SEQ ID NO:26, and SEQ ID NO:40 through to SEQ ID NO:46, inclusive or degenerates thereof, may be introduced into cells to induce production of the EBP. In another method, mRNA transcripts encoding the EBP may be microinjected or otherwise introduced into cells to cause production of the encoded peptide. Translation of mRNA in cell-free extracts such as the reticulocyte lysate system also may be used to produce EBPs. Those skilled in the art also can readily follow known methods for isolating EBP. These include, but are not limited to, immunochromatography, HPLC, size-exclusion chromatography, and ion-exchange chromatography.

The EBP disclosed herein will be useful as is or as a lead compound for developing further EBP including ErbB2 antagonists. Other EBPs may be generated as variants of the EBPs described herein (as described above) or alternatively they may be produced in a more random fashion and identified via binding and, signaling assays in comparison with the EBP.

Known binding peptides, such as the EBP described herein, may be subjected to directed or random chemical modifications such as acylation, alkylation, esterification, amidification, etc. to produce structural analogs which may function as antagonists.

In an alternative approach, additional EBP can be rationally designed. One way of doing this involves modeling the binding site of ErbB2 complexed with or without, for example, a EBP, using X-ray crystallography or NMR or Raman spectroscopy. In addition, the successful use of computer-based algorithms to model binding sites is discussed in U.S. Pat. No. 5,741,713, the entire contents of which are incorporated by reference herein. The strategy usually involves computer-based structural modeling of the binding site including its conformation, reactive groups, and charge groups, and generally requires knowledge of the three-dimensional structure of the binding site obtained by X-ray crystallography or NMR or Raman spectroscopy. With this knowledge, the requirements for a useful antagonist such as that disclosed herein can be determined, and rational design of synthetic antagonists can follow.

Rational design of EBP variants can also be accomplished by comparing and contrasting the amino acid sequences of the peptides disclosed herein (i.e., SEQ ID NO:1 through to SEQ ID NO:13, and SEQ ID NO:33 through to SEQ ID NO:39, inclusive). A study of the amino acid sequence as well as a structural analysis and subsequent comparison with peptides which bind to other ErbB family members (e.g., ErbB4) and not ErB2, can elucidate the amino acid residues and three-dimensional conformation involved in the binding specificity. Random or directed mutation of the putative amino acid residues involved in the recognition and/or binding of the peptide to ErbB2 can help to identify further binding and inhibitory peptides, as described herein.

One of skill in the art will be familiar with methods for predicting the effect on protein conformation of a change in protein sequence, and can thus "design" a variant which functions as an antagonist according to known methods. One example of such a method is described by Dahiyat and Mayo in Science 278:82–87, 1997, which describes the design of proteins de novo. The method can be applied to a known peptide to vary only a portion of the amino acid sequence. By applying the computational methods of Dahiyat and Mayo, specific variants of the disclosed peptide can be proposed and tested to determine whether the variant retains a desired conformation and the ability to bind and potentially inhibit ErbB2. Similarly, Blake (U.S. Pat. No. 5,565,325) teaches the use of known structures to predict and synthesize variants with similar or modified function.

Other methods for preparing or identifying peptides which bind to a particular target are known in the art. Molecular imprinting, for instance, may be used for the de novo construction of macromolecular structures such as peptides which bind to a particular molecule. See, for example, Kenneth J. Shea, Molecular Imprinting of Synthetic Network Polymers: The De Novo synthesis of Macromolecular Binding and Catalytic Sites, TRIP Vol. 2, No. 5, May 1994; Klaus Mosbach, Molecular Imprinting, Trends in Biochem. Sci., 19(9) January 1994; and Wulff, G., in Polymeric Reagents and Catalysts (Ford, W. T., Ed.) ACS Symposium Series No. 308, pp 186–230, American Chemical Society (1986). One method for preparing mimics of EBPs involves the steps of: (i) polymerization of functional monomers around a known substrate (i.e., the template or in this case, the EBP) that exhibits a desired activity; (ii) removal of the template molecule; and then (iii) polymerization of a second class of monomers in the void left by the template, to provide a new molecule which exhibits one or more desired properties which are similar to that of the template. This method can be used to generate both peptide and non-peptide variants. Non-peptide variants can be comprised of compounds such as polysaccharides, nucleosides, drugs, nucleoproteins, lipoproteins, carbohydrates, glycoproteins, steroids, lipids, and other biologically active materials. This method is useful for designing a wide variety of biological mimics that are more stable than their natural counterparts, because they are typically prepared by the free radical polymerization of functional monomers, resulting in a compound with a nonbiodegradable backbone. Other methods for designing such molecules include, for example, drug design based on structure activity relationships which require the synthesis and evaluation of a number of compounds and molecular modeling.

In important embodiments, peptide variants are made and screened using the phage display technology described herein. Peptide variants can be synthesized using degenerate oligonucleotides which are biased for a sequence encoding a known amino acid sequence. In a preferred embodiment, the phage libraries are made using the Fuse5 vector. (Scott and Smith, 1990, 249:386–90; Smith and Scott, Methods Enzymol 1993, 217:228–57) These techniques are well known in the art.

EBPs can be synthesized from peptides or other biomolecules including but not limited to saccharides, fatty acids, sterols, isoprenoids, purines, pyrimidines, derivatives or structural analogs of the above, or combinations thereof, and the like. Also envisioned in the invention is the synthesis of ErbB2 specific binding molecules made from non-natural amino acids (as described herein), peptoids, random biooligomers (U.S. Pat. No. 5,650,489), benzodiazepines, diversomeres such as dydantoins, dipeptides, nonpeptidal peptidomimetics with a beta-D-glucose scaffolding, oligocarbamates or peptidyl phosphonates.

Many if not all of these compounds can be synthesized using recombinant or chemical library approaches. One advantage of using libraries for inhibitor identification is the facile manipulation of millions of different putative candidates of small size in small reaction volumes (i.e., in synthesis and screening reactions). A vast array of candidate agents can be generated from libraries of synthetic or natural compounds. Libraries of natural compounds in the form of bacterial, fungal, plant and animal extracts are available or can readily be produced. Natural and synthetically produced libraries and compounds can be readily modified through conventional chemical, physical, and biochemical means. Another advantage of libraries is the ability to synthesize binding molecules that might not otherwise be attainable using naturally occurring sources, particularly in the case of non-peptide moieties.

Methods for preparing libraries of molecules are known in the art and several libraries are commercially available. Libraries of interest in the invention include peptide libraries (including synthetic peptide libraries, phage display libraries, and peptides-on-plasmid libraries), polysome libraries, randomized oligonucleotide libraries (including aptamer libraries), chemical libraries, synthetic organic combinatorial libraries (including small molecule libraries), and the like.

Degenerate peptide libraries can be readily prepared in solution. Peptide libraries can also be in immobilized form as bacterial flagella display libraries or as phage display libraries. Peptide ligands can be selected from combinatorial libraries of peptides containing at least one amino acid. Alternatively, libraries can be synthesized from peptoids and non-peptide synthetic moieties. Agents that contain non-peptide synthetic moieties are less subject to enzymatic degradation compared to their naturally-occurring counterparts. The libraries can also comprise cyclic carbon or heterocyclic structure and/or aromatic or polyaromatic structures substitutions.

Small molecule combinatorial libraries may also be generated. A combinatorial library of small organic compounds is a collection of closely related analogs that differ from each other in one or more points of diversity and are synthesized by organic techniques using multi-step processes. Combinatorial chemistry libraries include a large number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

As stated herein, other EBP can be generated and identified by conventional screening methods such as phage display procedures (e.g., methods described in Hart, et al., J. Biol. Chem. 269:12468 (1994)). Hart et al. report a filamentous phage display library for identifying novel peptide ligands for mammalian cell receptors. In general, phage display libraries using, e.g., M13 or fd phage, are prepared using conventional procedures such as those described in the foregoing reference. The libraries display inserts containing from 4 to 80 amino acid residues. The inserts optionally represent a completely degenerate or a biased array of peptides. Peptides that bind selectively to the extracellular domain of ErbB2 are obtained by selecting those phages that express on their surface an amino acid sequence that recognizes and binds to ErbB2 or the extracellular domain of ErbB2. These phage then are subjected to several cycles of re-selection to identify the ErbB2-binding phage that have the most useful binding characteristics. The minimal linear portion of the sequence that binds to the extracellular domain of ErbB2 can be determined. Typically, phage that exhibit the best binding characteristics (e.g., highest affinity) are further characterized to identify the particular amino acid sequences of the peptides expressed on the phage surface and the optimum length of the expressed peptide to achieve optimum binding. Phage can also be negatively prescreened for their ability to bind to other ErbB family members. Preferably, the peptides bind specifically to ErbB2 extracellular domains and not to the other ErbB family members. Thus, negative prescreening of phage with other ErbB family members can enrich for phage of interest.

In certain embodiments, the libraries may have at least one constraint imposed upon the displayed peptide sequence. A constraint includes, e.g., a positive or negative charge, hydrophobicity, hydrophilicity, a cleavable bond, and the necessary residues surrounding that bond, one or more cysteines for producing a cyclic peptide and combinations thereof. In certain embodiments, more than one constraint is present in each of the peptide sequences of the library. An example of an imposed constraint is the length of the peptide. In certain important embodiments, peptides that are 20 amino acids in length are preferred. An example of another imposed constraint is the presence of cysteine residues at or near the ends of the peptide. Generally, the presence of two cysteine residues in the peptide, provided they are sufficiently distant from one another, can result in a disulfide linked cyclic peptide structure.

The displayed peptide sequence can vary in size. As the size increases, the potential complexity of the library increases. It is preferred that the total size of the displayed peptide sequence (the random amino acids plus any spacer amino acids) should not be greater than about 100 amino acids long, more preferably not greater than about 50 amino acids long, and even more preferably not greater than about 25 amino acids long, and most preferably less than or equal to 20 amino acids long. The peptides may be as small as 3 amino acids in length, or 3–6 amino acids in length, or 6–8 amino acids in length.

ErbB2-binding molecules including peptides can be identified using a set of screening assays. Compounds such as library members can be screened for their ability to bind to ErbB2 in vitro using standard binding assays well known to the ordinary artisan and described below. ErbB2 may be presented in a number of ways including, but not limited to, cells expressing ErbB2 (such as ErbB2 overexpressing cell lines), isolated ErbB2, an isolated extracellular domain of ErbB2 or a fragment thereof, or a fusion protein of the extracellular domain and another protein such as an immunoglobulin or a GST fusion partner. Preferably, the ErbB2 domain is the extracellular domain of ErbB2. For some high throughput screening assays, the use of purified forms of ErbB2, its extracellular domain or a fusion of its extracellular domain with another protein may be preferable. Isolation of binding partners may be performed in solution or in solid state according to well-known methods.

Accordingly, the invention provides a method for screening a molecular library to identify a compound that inhibits interaction between ErbB2 and an EBP comprising an amino acid sequence selected from the group consisting of SEQ ID NO:1 through to SEQ ID NO:13, and SEQ ID NO:33 through to SEQ ID NO:39, inclusive, or functional equivalents thereof. The method generally involves performing a first assay between ErbB2 and the EBP to obtain a first assay result; performing a second assay between ErbB2 and the EBP in the presence of a molecular library member to obtain a second assay result; and comparing the first and second assay results to determine whether the molecular library member inhibits the interaction between ErbB2 and the EBP.

The assay may be a binding assay and it may be performed in vitro or in vivo. The assay may alternatively be a signaling assay. The method may involve the initial step of selecting a molecular library suspected of containing an ErbB2-binding molecule. In still other embodiments, the assay may be a phosphorylation assay such as that described in the Examples.

Such a selection process may involve using libraries which are made with the preferred constraints mentioned herein. In order to increase the ErbB2 specificity of a library, the library may be pre-screened by exposing it to a cell population that does not express ErbB2. In this way, binding partners which are not specific for ErbB2 can be eliminated or at least reduced in number from the library prior to further screening. Procedures for pre-screening include but are not limited to affinity column purification or biopanning.

Standard binding assays are well known in the art, and a number of these are suitable in the present invention including ELISA, competition binding assay (particularly suitable in the present invention since the EBP of the invention may be used), sandwich assays, radioreceptor assays using radioactively labeled ErbB2-binding peptides (wherein the binding is blocked in the presence of the library member), labeled in vitro protein-protein binding assays, electrophoretic mobility shift assays, immunoassays, cell-based assays such as two- or three-hybrid screens, etc. For example, two-hybrid screens are used to rapidly examine the effect of transfected nucleic acid molecules on the binding of ErbB2 to EBPs of the invention. The transfected nucleic acid molecules can derive from, for example, nucleic acid libraries. Convenient reagents for such assays, e.g., GAL4 fusion proteins, are known in the art. The nature of the assay is not essential provided it is sufficiently sensitive to detect binding of a small number of library members, although this sensitivity may not be as necessary for phage display based binding assays.

A variety of other reagents also can be included in the binding mixture. These include reagents such as salts, buffers, neutral proteins (e.g., albumin), detergents, etc. which may be used to facilitate optimal protein-protein and preferably protein-peptide binding. Such a reagent may also reduce non-specific or background interactions of the reaction components. Other reagents that improve the efficiency of the assay may also be used. The mixture of the foregoing assay materials is incubated under conditions under which the ErbB2 is normally found. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between ErbB2 and the EBP of the invention can be detected by any convenient method available to the user.

Typically, a plurality of assay mixtures are run in parallel with different compound or library member concentrations to obtain a different response to the various concentrations. One of these concentrations serves as a negative control, i.e., at zero concentration of the compound or at a concentration of compound below the limits of assay detection.

For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., columns or gels of polyacrylamide, agarose or sepharose beads, microtiter plates, microbeads, resin particles, etc. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

One of the components usually comprises, or is coupled to, a detectable label. A detectable label is a moiety, the presence of which can be ascertained directly or indirectly. Generally, detection of the label involves an emission of energy by the label. The label can be detected directly by its ability to emit and/or absorb light of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. Those of ordinary skill in the art will know of other suitable labels for binding to the binding partners used in the screening assays, or will be able to ascertain such, using routine experimentation. Furthermore, the coupling of these labels to the binding partners used in the screening assays of the invention can be done using standard techniques common to those of ordinary skill in the art.

The label may be bound to a library member, or incorporated into the structure of the library member. ErbB2 (or the extracellular domain of ErbB2), the EBP disclosed herein, or the candidate antagonist may be labeled by a variety of means for use in screening. In some embodiments, cells expressing ErbB2 may be used and the detectable label is conjugated to the EBP.

Another labeling technique which may result in greater sensitivity consists of coupling the binding partners to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

One example of a suitable binding assay involves the use of ErbB2, an extracellular domain of ErbB2 or an ErbB2 fusion protein immobilized on resin beads contained within a column or as a slurry in test tubes. This can be achieved by using a glutathione-S-transferase (GST) fusion of ErbB2 or its extracellular domain and a column containing anti-GST antibody. The ErbB2-GST fusion polypeptide is first immobilized on the column or resin, followed by the addition of a suspension of candidate antagonists such as, for example, library members, in a solution compatible with the binding of EBPs disclosed herein to the extracellular domain of ErbB2. The column is then washed to remove any residual non-bound compounds. The bound compounds are then eluted by changing the conditions on the column such that binding to the ligand binding site is no longer favored, such as pH or ionic concentration change, or competitive elution with reduced glutathione. The eluate is collected and the compounds contained therein are further analyzed. In the case where the compounds are peptides, the eluted peptides can be sequenced using standard Edman degradation amino acid sequencing techniques or in the case of non-peptide moieties, the eluted compounds are analyzed by standard analytical techniques such as HPLC and mass spectroscopy. Apparati for performing Edman degradation sequencing, an example of which is the Applied Biosystems 477A Protein Sequencer, are available commercially. Analysis of lead candidates from such binding assays using NMR spectroscopy are described in U.S. Pat. No. 5,877,030, the contents of which are incorporated herein by reference. In this way, the sequence or composition of the compounds which bind to the column can be deduced.

In other embodiments, it is preferred that ErbB2 is produced in eukaryotic expression systems such as insect or COS cells which can result in more suitable folding and glycosylation of the peptide.

A second criteria for testing a putative EBP is its ability to inhibit signal transduction involving ErbB2. One way in which EBPs can inhibit ErbB2 mediated signal transduction is by interfering with the ability of ErbB2 to interact with other signaling factors. As used herein, signaling factors are proteins or polypeptides that are involved in transducing a signal into or within a cell. Signaling factors include endogenous signaling factors which interact with ErbB2 to transmit a signal to ErbB2 or to accept a signal from ErbB2. As used herein, an "endogenous" molecule is one that is known to exist naturally in a cell and includes intracellular and transmembrane molecules. Examples of endogenous signaling factors include tyrosine kinases, phosphatases and adaptor proteins. Tyrosine kinases include receptor tyrosine kinases and non-receptor tyrosine kinases. Receptor tyrosine kinases include, but are not limited to, EGRF, ErbB3, ErbB4 (HER4), PDGFR, CSF-1R (c-fms), c-kit, LET-23R, HGFR/SFR (c-met), FGFR, IGF1R, flt3/flk2, flk1, c-ret, EphA2, TrkB (BDNFR), tek/tie2, stk, flt-1 (VEGFR), RON, TrkA (NGFR), MuSK, VEGFR2, ROR, tie 1, etc. Non-receptor tyrosine kinases include, but are not limited to, Fyn, Lck, Lyn, Syk/ZAP-70, Src, Yes, Hck, Blk, Yrk, Fgr, Rak, Brk, and Csk. Still other molecules lack tyrosine kinase activity but are still capable of being phosphorylated by a tyrosine kinase. Molecules can be phosphorylated by virtue of the fact they contain a tyrosine, a serine or a threonine residue which can be phosphorylated. Depending upon the embodiment of the invention, these molecules may or may not be phosphorylated. Receptor tyrosine kinases may be ligand-activated or not activated. In some preferred embodiments, the signaling factors are selected from the group consisting of Ras, Raf, MAPK, PI3K, and adaptor proteins such as Grb2 and Grb7. In the screening assays described herein, the ErbB2 specific signaling factors may be Grb2 or Grb7, or it may be an antibody or an antibody fragment specific for ErbB2 such as Herceptin® (Trastuzumab) (Genentech, South San Francisco, Calif.). Other ErbB2 specific antibodies are commercially available from Oncogene Research, Santa Cruz Biotechnology, and Nova Castra.

ErbB2 is known to be phosphorylated during signal transduction. Phosphorylation status of ErbB2 (such as, for example, at the Ser 1113 residue) therefore can be used as a readout for a signaling assay. As shown in the Examples, phosphorylation of tyrosine residues 877 and 1248 can also be used as a readout in a signaling assay. Phosphorylation of these residues is indicative of ErbB2 activation.

Binding interactions between ErbB2 and factors with which it interacts can also be carried out through the use of cell-based assays. As example of this is immunoprecipitation of such ErbB2 interacting factors from cell lysates using purified ErbB2 in the presence and absence of putative antagonists.

Binding assays can be followed by screens for biological antagonist activity. To be useful, the ErbB2 antagonist binds to ErbB2, precludes or inhibits binding of ErbB2 to one or more of its endogenous ligands and, in doing so, prevents, inhibits or interferes with signal transduction from ErbB2 and events downstream of such signaling. An example of an event downstream of signaling may be cell proliferation. One way of measuring cell proliferation involves the use of the MTT and BrdU proliferation assays. Alternatively, in vitro clonogenic assays can be used. These assays can be performed using either cell lines known to express a functional ErbB2 (such as SKBR3, BT474, SKOV3 or MDA361) or other cells which have been manipulated (i.e., transfected) to express ErbB2 (such as ErbB2 transfected NIH3T3 cells). Control cell lines that express no or low levels of ErbB2 include HBL100, MDA468 and MCF7. The peptides can also be tested for their ability to inhibit anchorage independent growth in the cancer cells.

The number and quality of colonies can be determined as a function of the presence and absence of the library member. Preferably, the assays are carried out by culturing the cells in a semi-solid culture under conditions which stimulate maximal colony growth from the cell population. The library member is then titrated into the cultures in order to determine the amount necessary to reduce colony formation. In this manner, in addition to the amount of antagonist necessary to inhibit colony growth altogether, one can also determine that amount which inhibits the growth by a particular percentage. In this way, the amount of antagonist which impacts upon colony growth from, for example, aggressive ErbB2-expressing cell lines, but not on the growth of less aggressive non-ErbB2-expressing cell lines can be determined. For example, it may be desirable to reduce colony growth of ErbB2-expressing cell lines by the maximum amount possible while leaving colony growth by non-ErbB2-expressing cell lines unaffected. Clonogenic assays such as those described herein are routinely employed by artisans of ordinary skill. (DeFriend et al., 1994, Br. J. Cancer, 70(2):204–11; Glinsky et al., 1996, Clin. Exp. Metastasis, 14(3):253–67; Shen et al., 1998, Oncol. Res. 10(6):325–31; Perez et al., 1998, Cancer Chemother. Pharmacol. 41(6):448–52) Moreover, each of the aforementioned in vitro screening assays is amenable to high-throughput screening.

Cells useful in these in vitro clonogenic assays are cell lines or primary cells which preferably are known to express ErbB2 and one or more of its endogenous ligands. Examples include breast cancer cell lines such as BT474, SKBR3, SKOV3 and MDA361. Cells which are genetically manipulated to overexpress ErbB2 are also useful in the invention. Cell lines which can be so manipulated are preferably breast cancer cell lines, but are not so limited, and include transfected NIH3T3. A control breast cell line which can be used is MDA468, MCF7 or HBL100. A control cell line for the manipulated cell line is NIH3T3.

Other measures of biological activity include the MTT assay and signaling assays such as phosphorylation assays. U.S. Pat. No. 6,123,939 describes both assays in the context of ErbB2 expressing cells.

Another way of measuring the biological antagonist activity of the synthetic compound is to perform in vivo assays in which the putative antagonist is introduced into animals, preferably mice, which have been made susceptible to, for example, breast cancer tumors. The mice are then analyzed to determine whether the putative antagonist ameliorates the symptoms of, for example, the cancer (e.g., a reduction in tumor growth). As an example of such an animal model, nude mice can be transplanted with human breast cancer xenografts, following which the growth of such grafts can be determined in the presence and absence of peptide administration. In some instances, breast tissue may also be harvested and plated into a clonogenic assay. Preferably the size of tumors in vivo and/or the number and quality of colonies derived from test animals should be compared to that of animals injected with control carrier (i.e., saline) lacking the putative antagonist. Adverse side effects can also be tested in animals injected with putative antagonists in this manner. Examples of such in vivo mouse models of breast cancer have been described by Gabri et al., 1999 Pathobiology 67(4):180–5; Liu et al., 1999 Am. J. Pathol. 155(6): 1861–7; and Vodovozona et al., 2000 Eur. J. Cancer 36(7): 942–9. These assays are also suitable for the testing of peptide-cytotoxic agent conjugates described herein.

The antagonists generated as described herein can also be screened in vivo or in vitro for the ability to prevent metastasis, using two different animal models of cancer, B16BL6 and LLC. Divino et al. (2000 Breast Cancer Res. Treat. 650(2):129–34.) specifically describe a mouse model of breast cancer metastasis. In some embodiments of the invention, the antagonists can be screened according to their ability to prevent invasion of tumor cells across a barrier. The barrier for the tumor cells may be an artificial barrier in vitro or a natural barrier in vivo. An in vivo barrier refers to a cellular barrier present in the body of a subject.

In vitro barriers include but are not limited to extracellular matrix coated membranes, such as Matrigel. Thus the putative antagonists can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378–383, provided the cells used in the assay have been characterized as having abnormal interaction of ErbB2 and its ligands. Matrigel is a reconstituted basement membrane containing type IV collagen, laminin, heparan sulfate proteoglycans such as perlecan, which bind to and localize bFGF, vitronectin as well as transforming growth factor-β (TGF-β), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference.

As alluded to earlier, the invention also embraces isolated nucleic acid molecules that code for EBP of the invention. As will be appreciated by one of ordinary skill in the art, a number of nucleic acid molecules code for each EBP, due to the degeneracy of the genetic code. For example, while the nucleic acid molecule having the nucleotide sequence SEQ ID NO:14 encodes EBP-1, there are multiple other nucleic acid molecules that also encode EBP-1. For example, the threonine residues can each be independently coded by the following codons: ACU, ACC, ACA and ACG. Each of the four codons is equivalent for the purposes of encoding an threonine residue. Thus, it will be apparent to one of ordinary skill in the art that any of the arginine-encoding nucleotide triplets may be employed to direct the peptide synthesis apparatus, in vitro or in vivo, to incorporate an arginine residue into a EBP. Thus, although SEQ ID NO:14 uses only the first of these codons, it is to be understood that the invention embraces nucleic acid molecules which use any of the six codons to code for threonine. Similarly, the invention embraces nucleic acid molecules that use any of the four codons coding for valine (GUU, GUC, GUA, and GUG), or either of the two codons coding for glutamine (CAA, CAG), or either of the two codons coding for glutamic acid (GAA, GAG), or either of the two codons coding for cysteine (UGU, UGC), or either of the two codons coding for lysine (AAA, AAG), or either of the two codons coding for tyrosine (UAU, UAC), or any of the six codons coding for leucine (UUA, UUG, CUU, CUC, CUA, and CUG), or either of the two codons coding for aspartic acid (GAU, GAC), or either of the two codons coding for asparagine (AAU, AAC), or any of the four codons coding for glycine (GGU, GGC, GGA, and GGG), or either of the two codons coding for phenylalanine (UUU, UUC), or either of the two codons coding for histidine (CAU, CAC), or any of the four codons coding for proline (CCU, CCC, CCA, CCG), or any of the six codons coding for arginine (CGU, CGC, CGA, CGG, AGA, and AGG), or any of the six codons coding for serine (UCU, UCC, UCA, UCG, AGU, and AGC), or any of the four codons coding for alanine (GCA, GCU, GCC, and GCG), or any of the three codons coding for isoleucine (AUU, AUC, and AUA). Methionine and tryptophan are each coded by a single codon respectively.

Putative nucleic acids sequences that encode the EBPs of the invention include TGG backbone with nucleic acid bases). In some embodiments, the nucleic acids are homogeneous in backbone composition. The purines and pyrimidines of the nucleic acids may also be substituted e.g., base analogs such as C-5 propyne substituted bases (Wagner et al., *Nature Biotechnology*

```
ACT GGT TGG TGT TTA AAT CCT GAA GAA TCT ACT TGG GGT TTT TGT ACT GGT TCT TTT;       (SEQ ID NO:14)

GTT GTT GCA TGT TCT TCG GAT TCG ACT ATG GGT GCA GTT GTT TGT TAT GAA CGT ATT;       (SEQ ID NO:15)

GGT TTT TGG ACT TGT GAA TAT GAT TGG TGG TCT GAT GCA ACT GTT TGT ATG CAT ACT TTA;   (SEQ ID NO:16)

GGT CGT GGT TGG TGT TGG TCT GAA TGG CAA AAT GAT TGG TTT TGG TGT TGG GAT CTT TGG;   (SEQ ID NO:17)

TGG ACT GGT TGG TGT TTA AAT CCT GAA GAA TCT ACT TGG GGT TTT TGT ACT GGT TCT TTT;   (SEQ ID NO:18)

GCA CGT TTA CAA TGT TGG TCT TTA GGT TGG GGT GGT CCT GTT TAT TGT GGT TTT GGT CAA;   (SEQ ID NO:19)

ATT CAA GAA GTT TGT TGG TTT GAT TAT AAT TTA TCT CAA TGG CAT TGT ATG ACT GTT ATT;   (SEQ ID NO:20)

CCT GAT ATT TAT TGT TTA TCT GTT ACT GCA CCT GGT TTT TTA ATT TGT TAT GAA CGT TAT;   (SEQ ID NO:21)

CAT GAT GAA TTA TGT GTT TTT TCT TTT GAT TTT AAT GCA TTA TTA TGT TGG CCT GCA GAA;   (SEQ ID NO:22)

TTA AAT TGG GAA TGT TGG TAT GAT TAT CGT TTA GAA GCA TGG GAT TGT CGT GGT GAT ATT;   (SEQ ID NO:23)

TGT GAA GTT TGG GGT GAA GTT CCT TGG ACT TGT;                                       (SEQ ID NO:24)

TGT GAA GTT TGG GGT TTT GTT CCT TGG GCA TGT;                                       (SEQ ID NO:25)

TCT AAT GAA TCT TGT GGT TCT CCT ATT AAT CCT TGG GGT GAA ATG TGT TTA TTA ATG TTA;   (SEQ ID NO:26)

TGG ACT GGT TGG TGT TTA AAT CCT GAA GAA TCT ACT TGG GGT TTT TGT CGT TCT GCA GGT;   (SEQ ID NO:40)

TGG ACT GGT TGG TGT TTA TCT CCT GAA GAA TCT ACT TGG GGT TTT TGT CGT TCT GCA GGT;   (SEQ ID NO:41)

TGG ACT GGT TGG TGT TTA AAT CCT GAA GAA TCT ACT TGG GGT TTT TGT TCT GGT TAT ATT;   (SEQ ID NO:42)

TGG ACT GGT TGG TGT TTT GAT GAT AAT CAT TCT ACT TGG GGT TTT TGT ACT GGT TCT TTT;   (SEQ ID NO:43)

GAT ACT GAT ATG TGT TGG TGG TGG TCT CGT GAA TTT GGT TGG GAA TGT GCA GGT GCA GGT;   (SEQ ID NO:44)

TCT TTA GCA TTA TGT TTA TCT GAA GGT GTT TTA TTA GGT GCA GAT TGT CGT GTT TTA TTT;   (SEQ ID NO:45)

TGG TCT TCT ATG TGT GGT GAT CCT ACT ATT GCA GAT TGG TTA TGG TGT TTT TCT GAT GCA.  (SEQ ID NO:46)
```

The foregoing nucleic acid sequences are intended to be simply illustrative and it is to be understood that depending upon the subject, the codon usage for particular amino acids will change, and thus so will the nucleic acid sequence. The invention intends to embrace all degenerates of the foregoing sequences. Given the teachings provided herein as the level of skill in the art, one of ordinary skill can readily ascertain the nucleic acid sequences of all degenerates.

It is to be understood that although the codons and nucleotide sequences listed herein contain thymidine bases, codons and nucleic acid molecules in which thymidine is replaced with uracil are equally embraced by the invention. Similarly, modified nucleotides may also be used in any of the nucleic acid molecules of the invention provided their function is preserved (e.g., hybridization, ability to be cloned or transcribed, etc.). Examples of modified nucleotides include those with a modified base and/or sugar, those having backbone sugars which are covalently attached to low molecular weight organic groups other than a hydroxyl group at the 3' position and other than a phosphate group at the 5' position (e.g., a 2'-O-alkylated ribose group). In addition, modified nucleic acids may include sugars such as arabinose instead of ribose. The nucleic acids may be heterogeneous in backbone composition thereby containing any possible combination of polymer units linked together such as peptide-nucleic acids (which have an amino acid backbone with nucleic acid bases). In some embodiments, the nucleic acids are homogeneous in backbone composition. The purines and pyrimidines of the nucleic acids may also be substituted e.g., base analogs such as C-5 propyne substituted bases (Wagner et al., *Nature Biotechnology* 14:840–844, 1996). Purines and pyrimidines which can be incorporated into the nucleic acids of the invention include but are not limited to adenine, cytosine, guanine, thymine, 5-methylcytosine, 2-aminopurine, 2-amino-6-chloropurine, 2,6-diaminopurine, hypoxanthine, and other naturally and non-naturally occurring nucleobases, substituted and unsubstituted aromatic moieties.

As used herein with respect to nucleic acid molecules, the term "isolated" means separated from its native environment in sufficiently pure form so that it can be manipulated or used for any one of the purposes of the invention. Examples of isolated nucleic acids include those that are: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid molecule is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleic acid molecule sequence existing in its native state in its natural host is not. An isolated nucleic acid molecule may be substantially purified, but need not be. For example, a nucleic acid molecule that is isolated within a cloning or expression vector is not pure in that it may comprise only a tiny percentage of the material in the cell in which it resides. Such a nucleic acid molecule is isolated, however, as the term is used herein because it is readily manipulable by standard techniques known to those of ordinary skill in the art.

According to the invention, isolated EBP nucleic acid molecules include nucleic acid molecules which code for an ErbB2 binding peptide that binds to the extracellular domain of ErbB2 (e.g., EBP-1, EBP-2, EBP-3, EBP-4, EBP-5, EBP-6, EBP-7, EBP-8, EBP-9, EBP-10, EBP-11, EBP-12, EBP-13, EBP-14, EBP-15, EBP-16, EBP-17, EBP-18, EBP-19, or EBP-20 (or functionally equivalent fragments thereof)). These nucleic acid molecule may have a nucleotide sequence selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:40, SEQ ID NO:41, SEQ ID NO:42, SEQ ID NO:43, SEQ ID NO:44, SEQ ID NO:45, or SEQ ID NO:46. The nucleic acid molecules also include nucleic acid molecules that contain deletions, additions and substitutions of the above sequences that code for an EBP, nucleic acid molecules that differ from the above nucleic acid molecules in codon sequence due to the degeneracy of the genetic code (as described above), and (complements thereof.

Homologs and alleles of the EBP nucleic acid molecules of the invention may include naturally occurring peptides or proteins that bind to ErbB2 (i.e., ErbB2 ligands). These molecules can be identified by conventional homology search or hybridization techniques. Example of homologs and alleles are those endogenous nucleic acid molecules that code for a peptide that binds to ErbB2 (and particularly the extracellular domain of ErbB2), and that hybridize under stringent conditions to a nucleic acid molecule having, for example, a nucleotide sequence selected from the group consisting of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:40, SEQ ID NO:41, SEQ ID NO:42, SEQ ID NO:43, SEQ ID NO:44, SEQ ID NO:45, and SEQ ID NO:46. The term "stringent conditions" as used herein refers to parameters with which the art is familiar. Nucleic acid molecule hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15 M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1% SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of EBP nucleic acid molecules of the invention. The skilled artisan also is familiar with the methodology for screening phage, cells and libraries preferably peptide or aptamer libraries for expression of ErbB2 antagonists which then are isolated, followed by isolation of the pertinent nucleic acid molecule and sequencing.

In general homologs and alleles typically will share at least 75% nucleotide identity to any EBP nucleic acid molecules (e.g., SEQ ID NO:14 through to SEQ ID NO:26, and SEQ ID NO:40 through to SEQ ID NO:46, inclusive) and/or at least 90% amino acid identity to any EBP amino acid sequences (i.e., SEQ ID NO:1 through to SEQ ID NO:13 and SEQ ID NO:33 through to SEQ ID NO:39, inclusive). Preferably, homologs and alleles will share at least 85% nucleotide identity and/or at least 95% amino acid identity and, even more preferably, at least 95% nucleotide identity and/or at least 99% amino acid identity will be shared. The homology can be calculated using various, publicly available software tools developed by NCBI (Bethesda, Md.) that can be obtained through the internet at the NIH website. Exemplary tools include the BLAST system using default settings, available at the NCBI website on the internet. Pairwise and ClustalW alignments (BLOSUM30 and/or BLOSUM62 matrix settings) as well as Kyte-Doolittle hydropathic analysis can be obtained using the MacVetor sequence analysis software (Oxford Molecular Group). Watson-Crick complements of the foregoing nucleic acid molecules also are embraced by the invention.

The invention also provides isolated unique fragments of EBP nucleic acid molecules or complements thereof. A unique fragment is one that is a 'signature' for the larger nucleic acid molecule such as, for example, those encoding EBPs or those encoding endogenous ErbB2 ligands. For example, the unique fragment is long enough to assure that its precise sequence is found sparingly in molecules within the human genome. Those of ordinary skill in the art may apply no more than routine procedures to determine if a fragment is unique within the human genome. Unique fragments, however, exclude fragments completely composed of the nucleotide sequences of a published GenBank submission or other previously published sequences as of the date of the invention or the filing date of this application.

A fragment which is completely composed of a sequence described in a GenBank published sequence (as of the date of the invention or the filing date of this application) is one which does not include any of the sequences unique to the invention. Thus, a unique nucleic acid fragment must contain a nucleotide sequence other than the exact sequence of those in GenBank or fragments thereof (as of the date of the invention or the filing date of this application). The difference may be an addition, deletion or substitution with respect to all or part of the GenBank sequence or it may be a sequence wholly separate from the GenBank sequence.

Unique EBP nucleic acid fragments also include nucleic acid molecules that encode unique EBP peptide fragments, as described above. As one of ordinary skill will appreciate, these nucleic acid molecules will be varied given the degeneracy in the nucleic acid code, however, the sequence of these nucleic acid molecules is ascertainable with routine reference to a codon table.

Unique fragments can be used as probes in Southern and Northern blot assays to identify nucleic acid molecules which contain these nucleotide sequences, or can be used in amplification assays such as those employing PCR. Unique fragments also can be used to produce fusion proteins for generating antibodies or determining binding of the peptide fragments or for generating immunoassay components.

As will be recognized by those skilled in the art, the size of the unique fragment will depend upon its conservancy in the genetic code. Thus, some regions of EBP nucleic acid molecules (e.g., SEQ ID NO:14 through to SEQ ID NO:26, and SEQ ID NO:40 through to SEQ ID NO:46, inclusive (as well as degenerates thereof)), or complements thereof will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31, and 32 bases) or more, up to the entire length of the disclosed sequence. As mentioned above, this disclosure intends to embrace each and every fragment of each sequence listed, beginning at the first nucleotide, the second nucleotide and so on, up to 8 nucleotides short of the end, and ending anywhere from nucleotide number 8, 9, 10, and so on for each sequence listed, up to the very last nucleotide, provided the sequence is unique as described above. Taking into account the exclusion described above, virtually any segment of the region of, for example, SEQ ID NO 14, beginning at nucleotide 1 and ending at nucleotide 30, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

Most if not all of the characteristics of nucleic acid molecule unique fragments are shared with peptide unique fragments disclosed herein.

The invention also involves expression vectors coding for EBPs and fragments and variants thereof and host cells containing those expression vectors. As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. In some preferred embodiments, the expression system is a phage.

A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a marker or coding sequence and regulatory sequences are said to be "operably" joined when they are covalently linked in such a way as to place the expression or transcription of the coding sequence under the influence or control of the regulatory sequences. If it is desired that the coding sequences be translated into a functional peptide or polypeptide, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CCAAT sequence, and the like. Especially, such 5' non-transcribed regulatory sequences will include a promoter region which includes a promoter sequence for transcriptional control of the operably joined coding sequence. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered for EBP expression by the introduction of a heterologous nucleic acid molecule, usually DNA, encoding a EBP or fragment or a variant thereof into the cells. The heterologous nucleic acid molecules are placed under operable control of transcriptional elements to permit the expression of the heterologous nucleic acid molecules in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (Nuc. Acids Res. 18:5322, 1990), and its use in transfection experiments is disclosed by, for example, Demoulin (Mol. Cell. Biol. 16:4710–4716, 1996). Still another preferred expression vector is an adenovirus, described by Stratford-Perricaudet, which is defective for E1 and E3 proteins (J. Clin. Invest. 90:626–630, 1992). The use of the adenovirus as an Adeno.P1A recombinant is disclosed by Warnier et al., in intradermal injection in mice for immunization against P1A (Int. J. Cancer, 67:303–310, 1996).

It will also be recognized that the invention embraces the use of the above described EBP nucleotide sequence-containing expression vectors to transfect host cells. Virtually any cells, be these prokaryotic (e.g., E. coli), or eukaryotic (e.g., CHO cells, COS cells, yeast expression systems, and recombinant baculovirus expression in insect cells) which can be transformed with heterologous DNA or RNA, and which can be grown or maintained in culture, may be used in the practice of the invention. Especially useful are mammalian cells such as human, mouse, hamster, pig, goat, primate, etc., from a wide variety of tissue types, including primary cells and established cell lines. Specific examples include mammalian epithelial cells, fibroblast cells, and kidney epithelial cells, either as primary cells or cell lines. Cell-free transcription systems also may be used in lieu of cells.

As eluded to earlier, the EBP of the invention, and preferably the nucleic acid molecules that encode these peptides can be used to screen cells or peptide or nucleic acid libraries for naturally occurring EBP (i.e., ErbB2 ligands) with homology to the EBPs of the invention. Naturally occurring EBP may comprise or share homology with the amino acid sequences of SEQ ID NO:1 through to SEQ ID NO:13 or SEQ ID NO:33 through to SEQ ID NO:39, inclusive or functionally equivalent fragments thereof. Naturally occurring peptides or polypeptides with such homology may be identified through homology searches in protein and peptide databases (such as GenBank) or binding to antibodies specific for EBP. In this way, native, naturally occurring binding partners of ErbB2 may be identified. Polypeptides identified in the manner may be useful, for example, as ErbB2 antagonists or agonists as well as in elucidating the natural mechanism through which ErbB2 and its interactions are inhibited or stimulated respectively. Polypeptides which are identified in this manner can be isolated from biological samples including tissue or cell homogenates, or alternatively can also be expressed recombinantly in a variety of prokaryotic and eukaryotic expression systems by constructing an expression vector appropriate to the expression system, introducing the expression vector into the expression system, and isolating the recombinantly expressed protein. The invention also embraces the identification of ErbB2 agonists which can also be useful in the treatment of certain diseases, particularly those affecting tissues in which ErbB2 is believed to play a physiological role such as CNS tissues.

In addition, the nucleic acid molecules which code for naturally occurring EBP may have homology to the nucleic acid molecules which encode the EBPs of the invention (e.g., SEQ ID NO:14 through to SEQ ID NO:26, and SEQ ID NO:40 through to SEQ ID NO:46, inclusive). Naturally occurring nucleic acid molecules with such homology may be identified through stringent hybridization of the EBP nucleic acid molecules to cells (e.g., whole cell filter hybridization) or nucleic acid libraries (e.g., cDNA libraries), or by homology searching in nucleic acid sequence databases such as GenBank.

The peptides, and unique fragments thereof, may be used in the diagnostic or therapeutic methods of the invention either in a free form (i.e., unconjugated or not complexed with another compound), or conjugated form. In one aspect, the EBP can be used as homing molecules to allow specific delivery of particular agents to diseased tissue. These agents include detectable labels (e.g., imaging agents) and therapeutic agents (e.g., cytotoxic agents such as anti-cancer agents).

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment be of such a nature that it does not impair substantially the effectiveness of either entity. Keeping these parameters in mind, any linkage known to those of ordinary skill in the art may be employed, covalent or noncovalent. Covalent is preferred. Noncovalent methods of conjugation may also be used. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

Conjugation of the EBP to a detectable label facilitates, among other things, detection of cells and tissues that overexpress ErbB2, and subsequent diagnosis. These agents can be imaging agents such as contrast agents and radioactive agents that can be detected using medical imaging techniques such as nuclear medicine scans and magnetic resonance imaging (MRI). Detectable labels for magnetic resonance imaging (MRI) include Gd(DOTA); for nuclear medicine include $^{201}$Tl, gamma-emitting radionuclide 99 mTc; for positron-emission tomography (PET) include positron-emitting isotopes, (18)F-fluorodeoxyglucose ((18) FDG), (18)F-fluoride, copper-64, gadodiamide, and radioisotopes of Pb(II) such as 203Pb, and 111In. In other embodiments, the peptides can also be conjugated or coupled to the surface of gas filled particles which can be detected using ultrasound.

In one particularly important aspect of the invention, the peptides are used to identify, isolate and remove cells that overexpress ErbB2 from a tissue or a cell population. As an example, the peptides can be used to remove breast cancer cells from a bone marrow population. Breast cancer patients often undergo autologous bone marrow transplantation following aggressive marrow-ablative chemotherapy and/or radiation therapy in order to reconstitute their marrow. Due to the autologous nature of these transplants there exists a possibility of re-administering cancer cells into the patient by way of the transplant. "Purging" of the marrow (i.e., removal of the cancer cells from the marrow cell population) prior to its re-infusion into the patient is generally recommended. The peptides of the invention can be used to identify and remove ErbB2 overexpressing cells. Separation or removal of ErbB2 expressing cells from the marrow population can be achieved using for example flow cytometry or panning. For flow cytometry purposes, the peptides should be labeled with a detectable label, preferably a fluorescent label, as described herein. The ability to purge marrow populations of, for example, breast cancer cells can reduce the recurrence of breast cancer metastases following transplant.

The EBP can also be conjugated to therapeutic agents. As used herein, a therapeutic agent is a compound that has been shown to have therapeutic benefit in a subject having a particular disorder. Therapeutic agents include cytotoxic agents (such as anti-cancer agents), immunomodulatory agents, anti-angiogenic agents, and translocation agents.

The EBP can be co-administered with therapeutic agents in an unconjugated form. In some embodiments, the EBP may be administered substantially simultaneously with another agent (e.g., an anti-cancer agent). By substantially simultaneously, it is meant that the EBP is administered to a subject close enough in time with the administration of the other therapeutic agent, so that the two compounds exert an additive or even synergistic effect.

One important category of therapeutic agents is cytotoxic agents. As used herein, a cytotoxic agent is an agent that can induce the death of a cell with which it is in contact. When conjugated to the EBP, the conjugate serves to deliver a cytotoxic agent directly and specifically to diseased cells (e.g., cancer cells). Prior art polypeptides including Herceptin have been co-administered with cytotoxic agents in clinical trials. Although the results of such trials have been promising, a smaller agent that binds to ErbB2 (such as the peptides of the invention) will be a significantly more effective therapeutic. In some instances, direct covalent linkage of the homing molecule and the cytotoxic agent will enhance the therapeutic effectiveness of both the peptide and the cytotoxic agent. Arap et al. (Science 279:377) have reported the ability of a small peptide generated using random peptide phage display technology and conjugated to doxorubicin to bind specifically to endothelial cells of tumor blood vessels. Administration of the novel peptide-doxorubicin conjugate to animals bearing breast cancer xenographs resulted in a dramatic increase in survival, with less associated toxicity than doxorubicin alone.

Chemotherapeutic agents that are useful in the invention in combination with the EBP include alkylating agents, antimetabolites, natural products, hormones and antagonists, and miscellaneous chemotherapeutic agents.

Alkylating agents include nitrogen mustards such as mechlorethamine ($HN_2$), cyclophosphamide, melphalan (L-sarcolysin), uracil mustard, chlorambucil; alkyl sulfonates such as busulfan; nitrosoureas such as carmustine (BCNU), lomustine (CCNU), semustine (methyl-CCNU), streptozocin (streptozotocin); triazenes such as dacarbazine (DTIC; dimethyltriazen-oimidazolecarbox-amide); platinum co-ordination complexes such as cisplatin (cis-DDP), carboplatin, tetraplatin, ipraplatin; and ethylenimine.

Antimetabolites include folic acid analogs such as methotrexate (amethopterin); pyrimidine analogs such as fluorouracil (5-fluorouracil; 5-FU) and cytarabine (cytosine arabinoside); purine analogs such as mercaptopurine (6-mercaptopurine; 6-MP) and thioguanine (6-thioguanine; TG).

Natural products include vinca alkaloids such as vinblastine (VLB), vincristine and vindesine; Epipodophyllo-toxins such as etoposide and teniposide; antibiotics such as dactinomycin (actinomycin D), daunorubicin (daunomycin; rubidomycin), doxorubicin, bleomycin, plicamycin (mithramycin), mitomycin (mitomycin C); and enzymes such as L-asparaginase.

Miscellaneous chemotherapeutic agents include substituted urea such as hydroxyurea; methyl hydrazine derivatives such as procarbazine (N-methylhydrazine, MIH); adrenocortical suppressants such as mitotane (o,p'-DDD) and aminoglutethimide.

Hormones and antagonists include adrenocorticosteroids such as prednisone; progestins such as hydroxyprogesterone caproate, medroxyprogesterone acetate, megestrol acetate; estrogens such as diethylstilbestrol and ethinyl estradiol; antiestrogens such as tamoxifen; and androgens such as testosterone propionate and fluoxymesterone.

Other cytotoxic agents are toxins such as diptheria toxin A chain, *P. aeruginosa* exotoxin A chain, ricin A chain, abrin A chain, modeccin A chain, α-sarcin, *Aleurites fordii* proteins, dianthin protein, *Phytolacca americana* proteins (PAPI, PAPII, PAP-S), *Momordica charantia* inhibitor, curcin, crotin, sapaonaria officinalis inhibitor, gelonin, mitogellin, restrictocin, phenomycin, enomycin, pokeweed antiviral protein, cholera toxin, pertussis toxin.

One particularly important class of cytotoxic agents is the anti-cancer agents. Anti-cancer agents are agents which possess a preferential cytotoxicity towards malignant cells. In some preferred embodiments, the anti-cancer agents are specific for cancers such as breast cancer, ovarian cancer, thyroid cancer, gastric adenocarcinoma, cervical cancer, prostate cancer, lung cancer, colorectal cancer, and salivary gland cancer. Some of these preferred anti-cancer agents include epirubicin, doxorubicin, taxol, taxanes (paclitaxel and docetaxel), vinorelbine, gemcitabine, capecitabine, cyclophosphamide, methotrexate, and fluorouracil.

Other examples of anti-cancer agents include but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel;

Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Taxol; Taxotere; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-cancer agents include:20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D;

spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating compounds include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and multiple drug resistance reducing compounds such as Cremaphor EL.

Other compounds which are useful in combination therapy for the purpose of the invention include the antiproliferation compound, Piritrexim Isethionate; the antiprostatic hypertrophy compound, Sitogluside; the benign prostatic hyperplasia therapy compound, Tamsulosin Hydrochloride; the prostate growth inhibitor, Pentomone; radioactive compounds such as Fibrinogen 1 125, Fludeoxyglucose F 18, Fluorodopa F 18, Insulin I 125, Insulin I 131, Iobenguane I 123, I Sodium I 131, Iodoantipyrine I 131, Iodocholesterol I 131, Iodohippurate Sodium I 123, Iodohippurate Sodium I 125, Iodohippurate Sodium I 131, Iodopyracet I 125, Iodopyracet I131, Iofetamine Hydrochloride I 123, Iomethin I 125, Iomethin I 131, Iothalamate Sodium I 125, Iothalamate Sodium I 131, Iotyrosine I 131, Liothyronine I 125, Liothyronine I 131, Merisoprol Acetate Hg 197, Merisoprol Acetate Hg 203, Merisoprol Hg 197, Selenomethionine Se 75, Technetium Tc 99m Antimony Trisulfide Colloid, Technetium Tc 99m Bicisate, Technetium Tc 99m Disofenin, Technetium Tc 99m Etidronate, Technetium Tc 99m Exametazime, Technetium Tc 99m Furifosmin, Technetium Tc 99m Gluceptate, Technetium Tc 99m Lidofenin, Technetium Tc 99m Mebrofenin, Technetium Tc 99m Medronate, Technetium Tc 99m Medronate Disodium, Technetium Tc 99m Mertiatide, Technetium Tc 99m Oxidronate, Technetium Tc 99m Pentetate, Technetium Tc 99m Pentetate Calcium Trisodium, Technetium Tc 99m Sestamibi, Technetium Tc 99m Siboroxime, Technetium Tc 99m Succimer, Technetium Tc 99m Sulfur Colloid, Technetium Tc 99m Teboroxime, Technetium Tc 99m Tetrofosmin, Technetium Tc 99m Tiatide, Thyroxine I 125, Thyroxine I 131, Tolpovidone I 131, Triolein I 125 and Triolein I 131.

Other agents that are suitable for use with the EBP described herein (whether in conjugated or unconjugated form) include, but are not limited to, small molecule quinazoline and pyrimidine-based inhibitors, and radioisotopes such as 212Pb. Cytotoxic agents can also be high energy-emitting radionuclides such as cobalt-60.

Other therapeutic agents that can be administered with the EBP (either unconjugated or unconjugated form) include immunomodulatory agents, apoptosis-inducing agents, and anti-angiogenic agents. An immunomodulatory agent is an agent which is capable of modulating an immune response, preferably at the tissue having the disorder. Immunomodulatory agents include adjuvants such as BCG, BCG cell walls, alum, DETOX, SYNTEX, *Corneybacterium parvum*, and immunostimulatory nucleic acids; and cytokines such as IFN-γ, IL-1, IL-2, and IL-6. Preferably the immunomodulatory agent is an immune response-inducing compound which induces an immune response at the tissue. In one embodiment, the immune response-inducing compound is a peptide. In another embodiment the immune response-inducing compound is a carbohydrate. As used herein an immune response-inducing or an immune response-inhibiting compound can be a peptide, a carbohydrate or some combination thereof. In some embodiments, the immunomodulatory agent is an antigen or an antigenic moiety capable of inducing an immune response.

An apoptosis-inducing agent is an agent that induces apoptosis of the cell with which it comes in contact, or in the cell within which it enters. An example of an apoptosis-inducing agent is described by Jodo et al. (J Biol Chem 2001 Aug. 23; epub). Other examples include curcumin, the chemotherapeutic agent suberoylanilide hydroxamic acid (SAHA), 7-hydroxystaurosporine, Indole-3-carbinol (I3C), bis(4,7-dimethyl-1,10 phenanthroline) sulfatooxovanadium (iv), and the like.

An anti-angiogenic agent is an agent which can inhibit angiogenesis, including inhibiting new blood vessel budding or growth of pre-existing vessels. Such agents are useful in restricting the blood supply to a diseased tissue or tumor. Anti-angiogenic agents include sulfated beta-cyclodextrins, sulfated malto-oligosaccharides, suramin, angiostatin, endostatin, fumagillin, non-glucocorticoid steroids, and heparin or heparin fragments, and antibodies to one or more angiogenic peptides such as αFGF, βFGF, VEGF, IL-8, and GM-CSF. Angiogenic inhibitory peptides such as the VEGF-R binding peptide reported by Binetruy-Toumaire et al. is also embraced by the invention as an anti-angiogenic agent. (Binetruy-Toumaire et al. EMBO J. 19:1525, 2000.)

The invention additionally provides methods which use the EBP disclosed herein. These methods include methods of diagnosis, including medical imaging, and methods of prevention and treatment of disorders characterized by ErbB2 overexpression. The invention seeks, in one aspect, to prophylactically or therapeutically treat subjects having or at risk of having a disorder characterized by ErbB2 overexpression. The method involves administering to a subject in need of such treatment (i.e., a subject who has been diagnosed as having or at risk of having the disorder) an EBP (such as EBP-1, EBP-2, EBP-3, etc.) or a functional equivalent thereof. The EBP or its functional equivalent is administered in an amount effective to inhibit the disorder. In preferred embodiments, the EBP is a peptide having an amino acid sequence selected from the group consisting of SEQ ID NO:1 through to SEQ ID NO:13 and SEQ ID NO:33 through to SEQ ID NO:39, inclusive. The peptides may be linear, but in some preferred embodiments, they are cyclic.

As used herein, a subject is a human, non-human primate, cow, horse, pig, sheep, goat, dog, cat or rodent. In all embodiments, human subjects are preferred.

ErbB2 overexpression is defined as a level higher than that observed in a control normal population as described herein. A "normal" level, as used herein in reference to the level of ErbB2 mRNA or polypeptide, may be a level in a control population, which preferably includes subjects having similar characteristics as the treated individual, such as age and sex. The "normal" level can also be a range, for example, where a population is used to obtain a baseline range for a particular group into which the subject falls. Thus, the "normal" value can depend upon a particular population selected. Preferably, the normal levels are those of apparently healthy subjects who have no prior history of ErbB2 overexpression related disorders. As an example, if the subject to be treated has been diagnosed as having breast cancer or is at risk of having breast cancer, then the control population is one that does not have breast cancer and is not at risk of having breast cancer (e.g., that does not have a family history of breast cancer). Such normal levels can then be established as preselected values, taking into account the category into which an individual falls. Appropriate ranges and categories can be selected with no more than routine experimentation by those of ordinary skill in the art. Either the mean or another preselected number within the range can be established as the normal preselected value.

More preferably, the normal level is that level in a tissue of a normal subject corresponding to the tissue sampled for the test subject. In other instances, the normal levels can also be determined by measuring mRNA and/or peptide or polypeptide levels in a sample of normal tissue adjacent to the suspected diseased tissue in the subject to be treated. As an example, breast tumors are, in some cases, sufficiently delineated to the extent that such tissue can be distinguished from the surrounding normal breast tissue. This delineation facilitates selective removal of diseased breast tissue, such as occurs in non-radical mastectomies (e.g., lumpectomy). Similarly, such delineation can be used in the present invention to harvest both suspected diseased tissue and normal tissue from a given subject.

The disorders to be prevented or treated according to the invention may occur in tissues in which ErbB2 is known to be expressed normally. ErbB2 is expressed during fetal development, particularly in neural tissue, however it is minimally expressed in normal adult tissue. Disorders to be prevented or treated may also occur in tissues in which ErbB2 expression has not been detected normally (e.g., most normal adult tissues). Tissues at risk of developing a disorder similarly include tissues in which the disorders listed herein have been found previously (e.g., breast and esophageal tissue).

Preferably, the disorder being diagnosed or treated is a proliferative disorder such as cancer. As used herein, a cancer is defined as an uncontrolled (e.g., factor independent) growth of abnormal cells, which can either remain localized, or may disseminate throughout the body via the bloodstream or the lymphatic system, and thereby seed a secondary site (i.e., a metastasis). The diagnostic, prophylactic, and treatment methods of the invention are intended to be used to in the prevention and treatment of primary tumors and secondary tumors (i.e., metastases). ErbB2 overexpression has been reportedly associated with particular forms of cancer including most notably breast cancer and ovarian cancer. Examples of cancers to be diagnosed, prevented, and/or treated include: biliary tract cancer; brain cancer, including glioblastomas and medulloblastomas; breast cancer; cervical cancer; choriocarcinoma; colon cancer; endometrial cancer; esophageal cancer; gastric cancer; hematological neoplasms, including acute lymphocytic and myelogenous leukemia; chronic lymphocytic and myelogenous leukemia; multiple myeloma; AIDS-associated leukemias and adult T-cell leukemia lymphoma; intraepithelial neoplasms, including Bowen's disease and Paget's disease; liver cancer; lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells, and mesenchymal cells; pancreas cancer; prostate cancer; colorectal cancer; sarcomas, including leiomyosarcoma, rhabdomyosarcoma, liposarcoma, fibrosarcoma, and osteosarcoma; skin cancer, including melanoma, Kaposi's sarcoma, basocellular cancer, and squamous cell cancer; testicular cancer, including germinal tumors (seminoma, non-seminoma teratomas, and choriocarcinomas), stromal tumors, and germ cell tumors; thyroid cancer, including thyroid adenocarcinoma and medullar carcinoma; and renal cancer including adenocarcinoma and Wilms' tumor. In some important embodiments, the cancer is defined as an ErbB2 expressing cancer such as breast cancer, lung cancer, ovarian cancer, gastric cancer and bladder cancer. Preferably, the invention is directed at breast cancer and esophageal cancer.

The EBP of the invention can also be used to prevent or inhibit metastasis. Tumor metastasis involves the spread of tumor cells primarily via the vasculature following the disassembly of tumor cell-extracellular matrix (ECM) interactions through, the degradation of the ECM, and tumor cell extravasation through the capillary bed. The invasion and metastasis of cancer is a complex process which involves changes in cell adhesion properties which allow a transformed cell to invade and migrate through the ECM and acquire anchorage-independent growth properties. Liotta, L. A., et al., Cell 64:327–336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

Subjects having the disorder characterized by ErbB2 overexpression include subjects who have a disorder such as cancer. These subjects may be identified using the diagnostic methods described herein, and/or the methods used to diagnose the cell proliferative disorders listed above, including physical exam and diagnostic imaging tests. The diagnosis of such disorders, including cell proliferative disorders such as cancer and metastasis, are well known in the art and are routinely practiced by medical professionals. The treatment method may further comprise the selection of a subject having the disorder prior to the administration of the ErbB2 antagonist, according to the teaching provided herein.

The prophylactic methods of the invention are directed to subjects who are at risk of developing the disorder. Such a subject may also be identified using the diagnostic methods provided herein. Namely, a subject at risk may be one who exhibits ErbB2 overexpression in a particular tissue yet who does not manifest other symptoms of the disorder (e.g., no discernible breast lump in the case of a subject at risk of breast cancer). Other subjects at risk of developing such a disorder may be those with a family history of such disorders. As an example, subjects with a family history of breast cancer may be considered subjects for prophylactic treatment. Subjects at risk of certain disorders characterized by ErbB2 overexpression may also be those who have previously been diagnosed and treated for such a disorder. An example of this is a subject who has previously been diagnosed and treated for breast cancer. This subject is at risk of re-developing breast cancer either as a primary tumor or as a metastasis at a secondary site. In certain embodiments, the prophylactic methods further comprise first selecting a subject who is at risk of developing the disorder prior to the administration of the EBP.

In still other aspects, the invention embraces the use of ErbB2 agonists as therapeutic agents, particularly in the treatment of disorder such as osteoporosis, paralysis, or degenerative nerve disease (e.g., Parkinson's disease). Such agonists can be identified via homology to the EBPs identified herein.

The EBP may have varying binding affinity for ErbB2. This variation can be exploited in the treatment of subjects where it is necessary to control the extent of ErbB2 inhibition desired either as a function of development or of time in a treatment regimen. Thus, early on in a subject's treatment it may be desirable to administer a higher affinity EBP while later in the treatment (for example, during a remission) it may be more suitable to administer a lesser affinity EBP. In addition, lower affinity EBP may also be desired in some instances in order to effect better solid tumor perfusion.

The EBP are administered to a subject in an effective amount. The effective amount will depend upon the mode of administration, the particular condition being treated, and the desired outcome. It will also depend upon, as discussed above, the stage and severity of the condition, the subject to be treated including the age and physical condition of the subject, the nature of concurrent therapy, if any, and like factors well-known to the medical practitioner. For prophylactic applications, it is generally that amount sufficient to delay the onset of, inhibit the progression of, or halt altogether the particular condition sought to be prevented. For therapeutic applications, it is generally that amount sufficient to achieve a medically desirable result.

When used therapeutically, an effective amount is that amount which inhibits the disorder. Such inhibition may be measured by an inhibition or a decrease in cell proliferation or, in some instances, tumor growth. Inhibition of tumor growth may be manifest as a reduction in the size of a tumor mass, or as a failure of the tumor to increase in size. Inhibition of the disorder may also be measured in terms of the occurrence and diminution of metastatic lesions in the subject. When used prophylactically, an effective amount may be that amount which prevents a disorder from arising. Such inhibition may be measured by an absence of a tumor, perhaps manifest as a failure of the suspect tissue to increase in size or mass, or to develop a discernible tumor. If the subject to be treated already has a tumor, and is at risk of having a metastasis, the effective amount may also be that amount which prevents the spread of a primary tumor to secondary sites (i.e., an inhibition in metastasis). Thus, in one embodiment, the agent may be administered in an effective amount to inhibit metastasis, independent of its ability to inhibit primary tumor growth.

Generally, doses of active compounds of the present invention would be from about 0.01 mg/kg per day to 1000 mg/kg per day. It is expected that doses ranging from 1–500 mg/kg, and preferably doses ranging from 1–100 mg/kg, and even more preferably doses ranging from 1–50 mg/kg, will be suitable.

The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion.

Intravenous or intramuscular routes are not particularly suitable for long-term therapy and prophylaxis. They could, however, be preferred in emergency situations. Oral administration may be preferred for prophylactic treatment because of the convenience to the patient as well as the dosing schedule.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the compounds, for example the ErbB2 binding capacity of the EBPs (see, for example, Sciarra and Cutie, "Aerosols," in *Remington's Pharmaceutical Sciences,* 18th edition, 1990, pp 1694–1712; incorporated by reference). Those of skill in the art can readily determine the various parameters and conditions for producing aerosols without resort to undue experimentation.

The EBPs, functional equivalents thereof and/or nucleic acid molecules that encode EBPs, may be administered directly to a tissue. Preferably, the tissue is itself a tumor or it is a tissue in which the disorder exists. Alternatively, the tissue is one in which a tumor or disorder is likely to exist. For example, a subject at risk of developing breast cancer may be prophylactically treated by administering an EBP into the breast tissue of the subject. Direct tissue administration may be achieved by direct injection. The EBPs may be administered once, or alternatively they may be administered in a plurality of administrations. If administered multiple times, the EBPs may be administered via different routes. For example, the first (or the first few) administrations may be made directly into the affected tissue while later administrations may be systemic. These later administrations may also comprise lower doses of EBP, particularly if their purpose is remission maintenance rather than remission induction.

Although the EBPs of the invention can act as targeting agents, it may also be desirable in some instances to conjugate an EBP to a particular targeting agent or compound such as a ligand specific for a particular tissue or tumor type. In this way, a subset of ErbB2 expressing cells can be targeted, and in some instances cells that express low levels of ErbB2 (i.e., levels insufficient to bind large amounts of EBP in an unconjugated form) can also be targeted. The agents of the invention may be targeted to primary or, in some instances, secondary (i.e., metastatic) lesions through the use of targeting compounds which preferentially recognize a cell surface marker. The targeting compound may be directly conjugated to the agents of the invention via a covalent linkage. The agent may be indirectly conjugated to a targeting compound via a linker. Methods of conjugation suitable in the invention have been described elsewhere herein.

Alternatively, the targeting compound (including the EBP) may be conjugated or associated with an intermediary compound such as, for example, a liposome within which the agent is encapsulated. Liposomes are artificial membrane vessels which are useful as a delivery vector in vivo or in vitro. It has been shown that large unilamellar vessels (LUV), which range in size from 0.2–4.0 μm can encapsulate large macromolecules. Liposomes may be targeted to a particular tissue, such as the vascular endothelium, by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235–241 (1985). In still other embodiments, the targeting compound may be loosely associated with the EBP, such as within a microparticle comprising a polymer, the EBP and the targeting compound.

In some instances, the EBP of the invention can exist on the surface of a liposome that contains a therapeutic agent. In this way, the EBP acts as a targeting agent that delivers the therapeutic agent to a cell that expresses ErbB2. The liposome may alternatively carry a nucleic acid sequence intended for use in gene therapy.

Targeting compounds useful according to the methods of the invention are those which direct the antagonist to a site of a disorder characterized by ErbB2 overexpression (e.g., a tumor). The targeting compound of choice will depend upon the nature of, for example, the tumor or the tissue origin of the metastasis. In some instances it may be desirable to target the agent to the tissue in which the tumor is located. As an example, agents can be delivered to breast epithelium by using a targeting compound specific for breast tissue. In important embodiments, the target is specific for malignant breast epithelium. Examples of compounds which may localize to malignant breast epithelium include, but are not limited to, estrogen and progesterone, among others. Ovarian cancers are also known to express EGFR and c-fms, and thus could be targeted through the use of ligands for either receptor. In the case of c-fms which is also expressed by macrophages and monocytes, targeted delivery to an ovarian cancer may require a combination of local administration such as a vaginal suppository as well as a targeting compound. Prostate cancers can be targeted using compounds such as peptides (e.g., antibodies or antibody fragments) which bind to prostate specific antigen (PSA) or prostate specific membrane antigen (PSMA). Other markers which may be used for targeting of the agent to specific tissues include, for example, in liver: HGF, insulin-like growth factor I, II, insulin, OV-6, HEA-125, hyaluronic acid, collagen, N-terminal propeptide of collagen type III, mannose/N-acetylglucosamine, asialoglycoprotein, tissue plasminogen activator, low density lipoprotein, carcinoembryonic antigen; in kidney cells: angiotensin II, vasopressin, antibodies to CD44v6; in keratinocytes and skin fibroblasts: KGF, very low density lipoprotein, RGD-containing peptides, collagen, laminin; in melanocytes: kit ligand; in gut: cobalamin-intrinsic factor, heat stable enterotoxin of *E. coli*; in breast epithelium: heregulin, prolactin, transferrin, cadherin-11. Other markers specific to particular tissues are available and would be known to one of ordinary skill in the art. In still other embodiments, the agent of the invention may be targeted to fibroblasts via ligands or binding partners for fibroblast specific markers. Examples of these markers include, but are not limited to fibroblast growth factors (FGF) and platelet derived growth factor (PDGF).

In still other embodiments, the invention provides bifunctional peptides that are capable of binding to ErbB2 as well as another protein such as for example EGFR, ErbB3 or ErbB4.

The invention further provides a composition of the EBPs or their functional equivalents for use as a medicament, methods for preparing the medicament, and methods for the sustained release of the medicament in vivo.

Pharmaceutical preparations of EBP (e.g., EBPs), functional equivalents thereof, and/or nucleic acid molecules encoding such EBP are provided by the invention. The pharmaceutical preparation also contain a pharmaceutically acceptable carrier. An EBP is present in the pharmaceutical preparation in a prophylactically or therapeutically effective amount.

The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being commingled with the agents of the present invention, and with each other, in a manner such that there is no interaction which would substantially impair the desired pharmaceutical efficacy.

The pharmaceutical preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

In yet other embodiments, the EBP is administered via a biocompatible microparticle or implant that is suitable for implantation into the mammalian recipient. Exemplary bioerodible implants that are useful in accordance with this method are described in PCT International Application No.

PCT/US/03307 (Publication No. WO95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly (hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly (ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581–587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the EBP or function equivalent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of having a disorder characterized by ErbB2 overexpression. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The following examples are included for purposes of illustration and are not intended to limit the scope of the invention.

EXAMPLES

Example 1

Identification of Peptide Phage from Random and Biased Peptide Phage Libraries

Clones were identified by screening random as well as biased peptide phage library. Peptides identified by screening random libraries include those having the following sequences:
CB022701-20(E-20) DTDMCWWWSREFGWECAGAG (SEQ ID NO:37)
CB051701-19 (C-19) SLALCLSEGVLLGADCRVLF (SEQ ID NO:38)
CB051701-25 (C-25) WSSMCGDPTIADWLWCFSDA (SEQ ID NO:39).

The following example describes the methodology used to identify four clones from four biased peptide phage libraries. The libraries were enriched for the sequence of the EC-1 phage clone (SEQ ID NO:1). The four libraries had the following design:
$X_4$CLNPEESTWGFCRSAG (SEQ ID NO:29),
WTGWCX$_5$STWGFCRSAG (SEQ ID NO:30),
WTGWCLNPEEX$_5$CRSAG (SEQ ID NO:31), and
WTGWCLNPEESTWGFCX$_4$ (SEQ ID NO:32),
where X=any amino acid.
The peptides so identified had the following sequences:
02–124 WTGWCLNPEESTWGFCRSAG (SEQ ID NO:33)
02–137 WTGWCLSPEESTWGFCRSAG (SEQ ID NO:34)
02–140 WTGWCLNPEESTWGFCSGYI (SEQ ID NO:35)
02–135 WTGWCFDDNHSTWGFCTGSF (SEQ ID NO:36).

Example 2

Peptide Phage Bind Specifically to Purified ErbB2 Extracellular Domain

The peptide libraries were screened for the ability to bind to the purified extracellular domain of ErbB2 with a His tag (denoted CBECD). The following example demonstrates the methodology for such screening. Binding results are shown in FIGS. 1A and 1B.

SfmECDAP labeled wells were plated with 250 ng of a purified ErbB2 ECD-alkaline phosphatase fusion protein; CBECD labeled wells were plated with 250 ng of a purified ErbB2 ECD-polyhistidine-tagged protein; bovine serum albumin (denoted BSA) was used as a negative target control. E12 and CB1 are peptide phage clones identified independently that display an identical (ErbB2-binding) peptide. E12CB1-NA peptide phage clones were constructed to present, with and without a glycine-glycine-alanine linker, a shortened form of the peptide. Results indicate that the deletion mutants were inactive (FIG. 1A). G78 is a peptide phage clone that binds strongly to the Grb7 SH2 domain, used here as a negative peptide phage control. Library phage also serve as a negative peptide phage control. 9G6 is an antibody to the ECD of ErbB2.

FIG. 1B demonstrates the binding to the extracellular domain of ErbB2 of the peptides identified from the biased libraries.

Example 2

Binding of Peptide Phage to Membrane Lysates From ErbB2 Expressing Cells

Figure 2A:
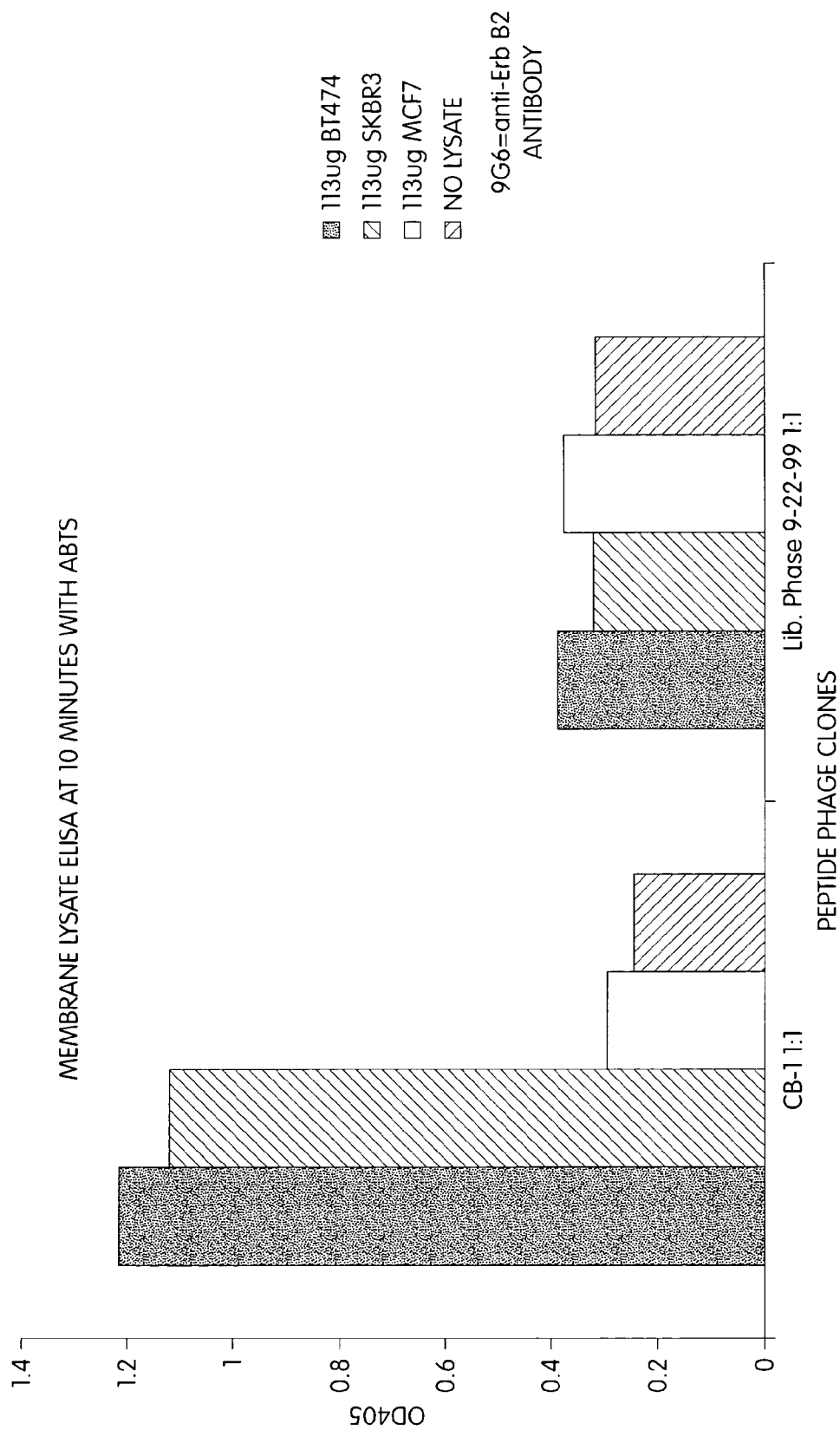
FIG. 2A is a bar graph showing ELISA results using membrane lysates and the CB1 peptide phage clone.

The above identified peptide phage specifically bind to native, intact ErbB2 extracted from the membranes of human breast cancer cells that overexpress ErbB2. Plates were coated with 1 μg of an antibody that binds to the intracellular domain of ErbB2, followed by 100 μl of solubilized membrane preparations from two different breast cancer cell lines that overexpress ErbB2 (BT474 and SKBR3), and probed with CB1 peptide-phage, control library phage, and 9G6 anti-ErbB2. MCF7 cells serve as a (relative) negative target control, as MCF7 breast cancer cells express only a low level of ErbB2. (See FIG. 2A.) The ELISA data indicates that the EBP gives a signal higher than the anti-ErbB2 antibody used as a positive control in the assay.

Figure 2B:
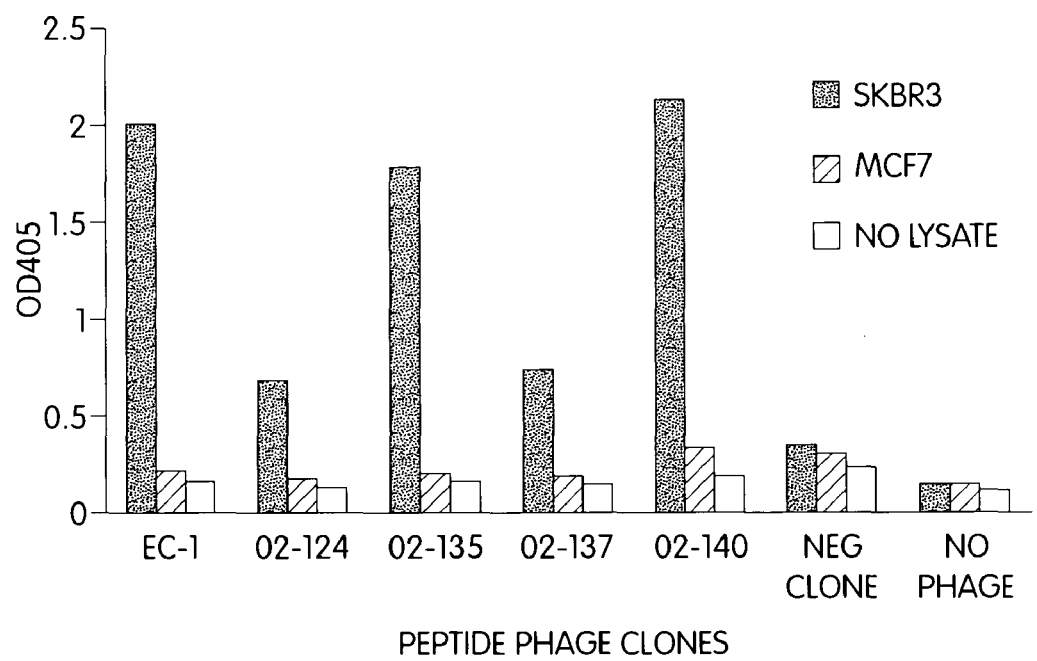
FIG. 2B is a bar graph showing ELISA results for EC-1 and new clones isolated from EC-1 biased phage display library showing binding to SKBR3 (which overexpress ErbB2) but not to MCF7 (which minimally express ErbB2) lysates. Buffer alone (no lysate) is the control. Additional negative controls include a negative phage clone and no phage (blocker only).

Peptide phage derived from the EC-1 biases library similarly bind specifically to membrane lysates from ErbB2 expressing SKBR3 cells but not to lysates from minimally expressing MCF7 cells. (See FIG. 2B.)

Figure 3:
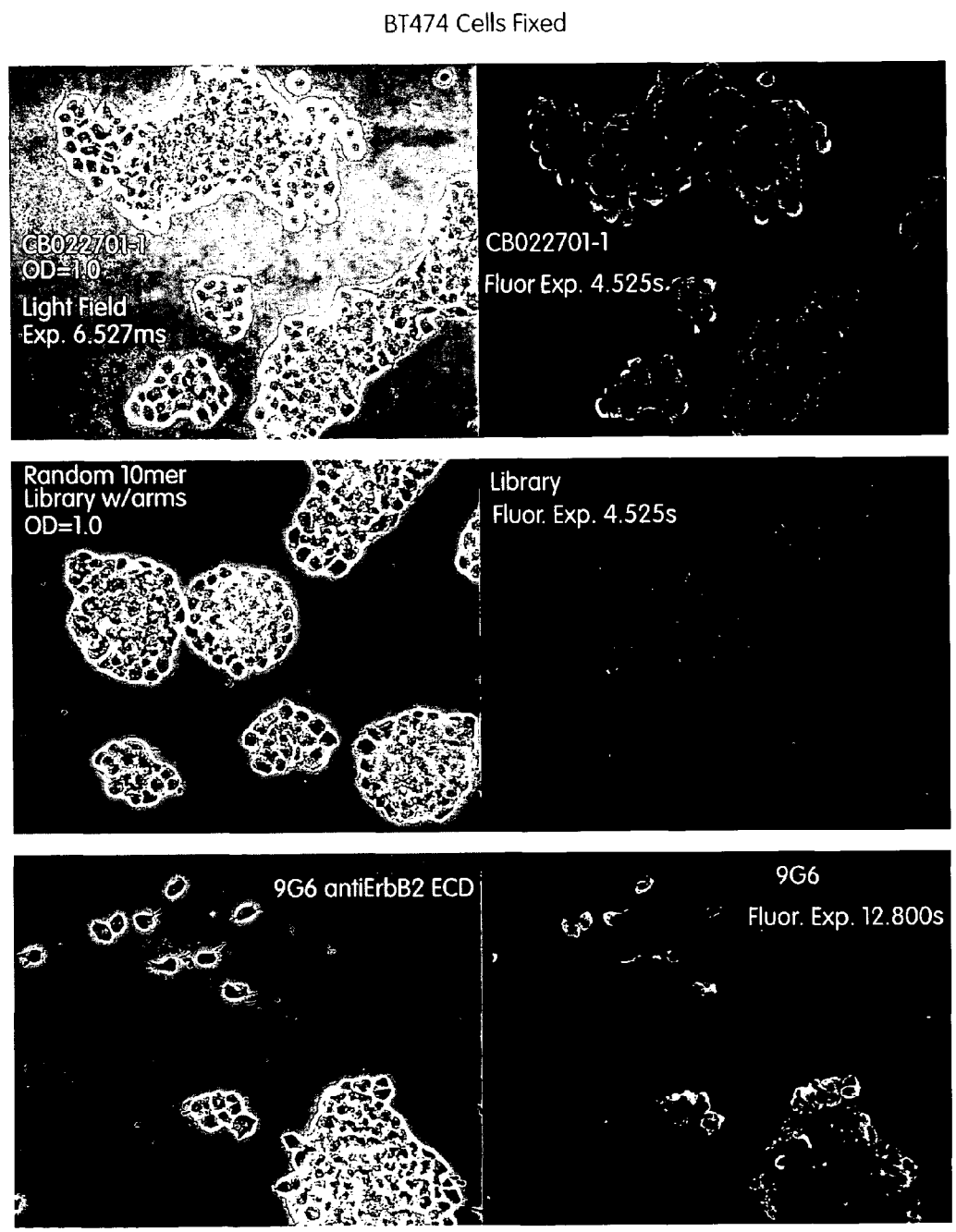
FIG. 3 is a series of photographs showing the ability of the peptide phage clones to bind to BT474 cells.
Figure 4:
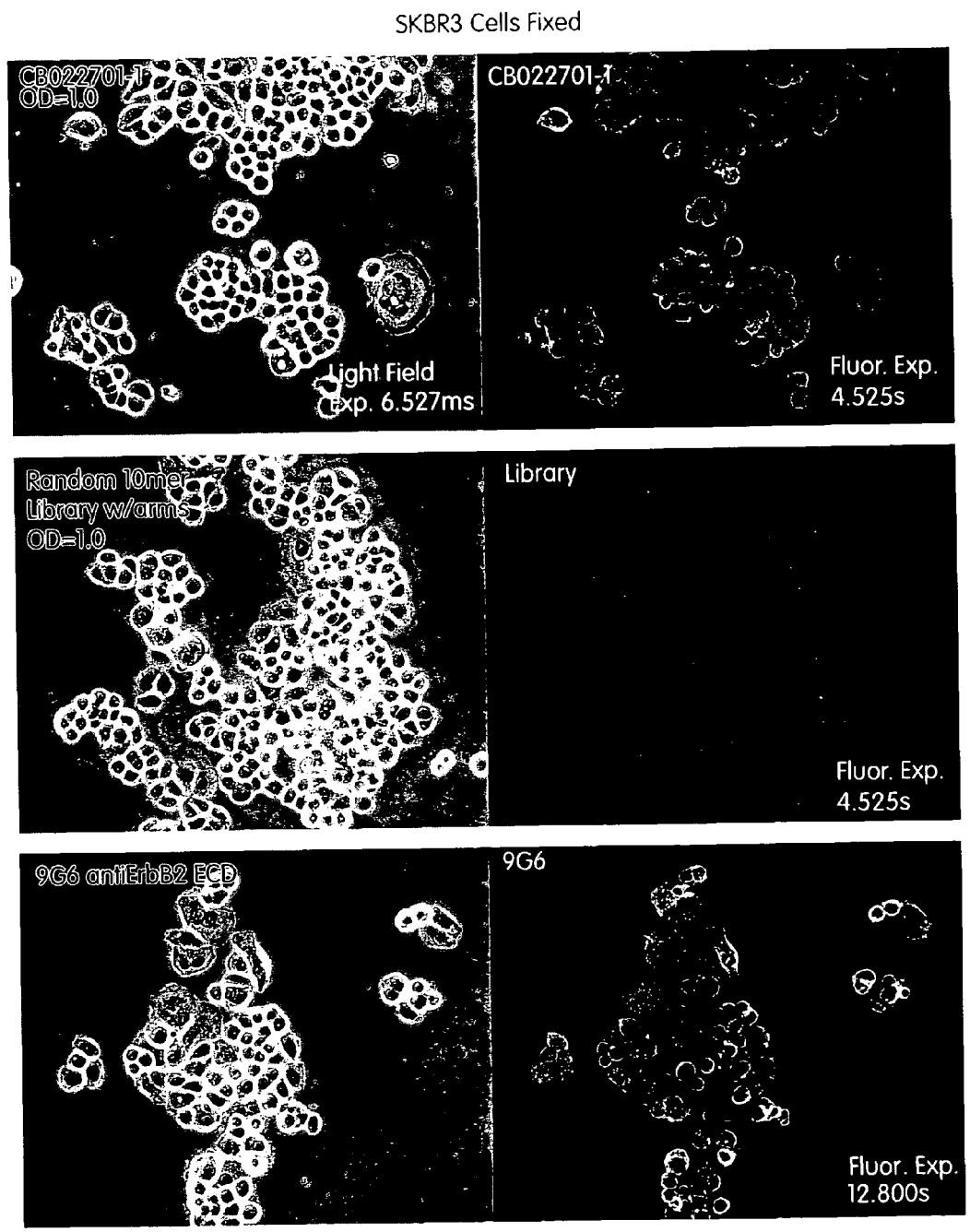
FIG. 4 is a series of photographs showing the ability of the peptide phage clones to bind to SKBR3 cells.
Figure 5:
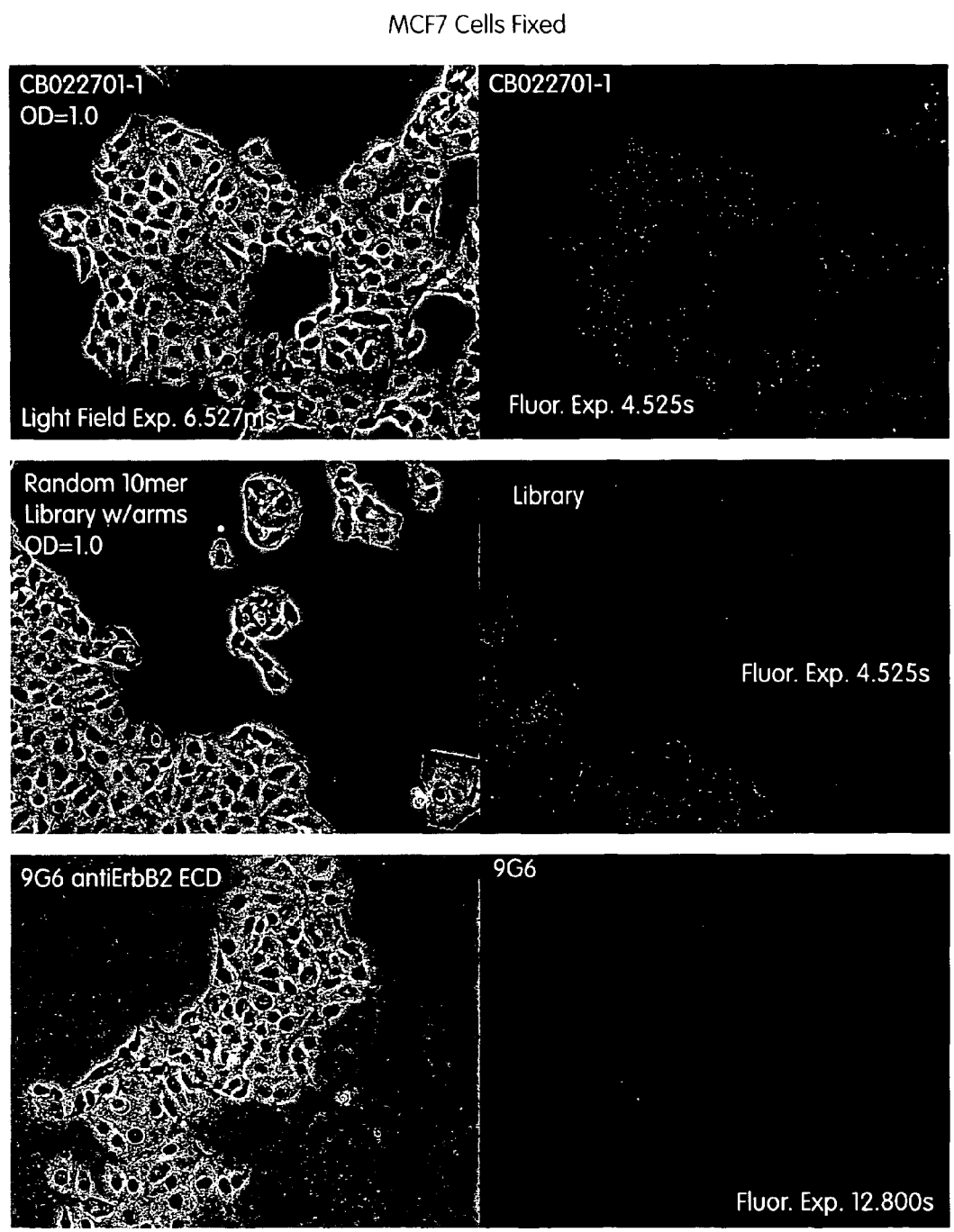
FIG. 5 is a series of photographs showing lack of peptide phage clone binding to MCF7 cells, which express only low levels of ErbB2.

Immunofluorescence assay results indicate that the peptide is a highly effective ErbB2-binding agent as demonstrated by the ability of phage bearing the peptide to label brightly the surface of ErbB2-overexpressing cells, but to not bind to cells that do not overexpress ErbB2 (FIGS. 3, 4, 5).

Example 3

Effect of Phage Peptide on ErbB2 Phosphorylation

Figure 6A:
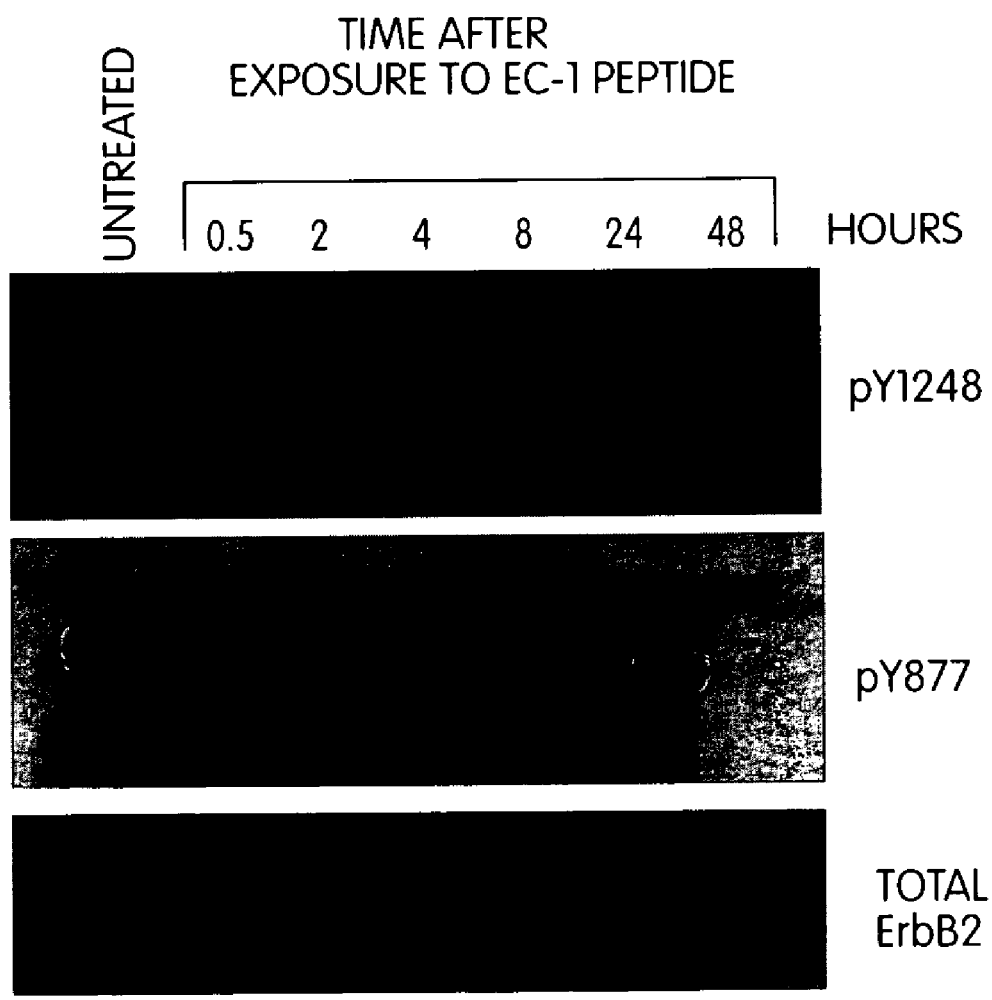
FIG. 6A is a Western blot analysis of SKBR3 cell lysates made at various times following 15 minute treatment with 25 μM EC-1 peptide. Blots were probed with pY1248 phospho ErbB2 antibody, pY877 phospho ErbB2 antibody and total ErbB2 antibody.
Figure 6B:
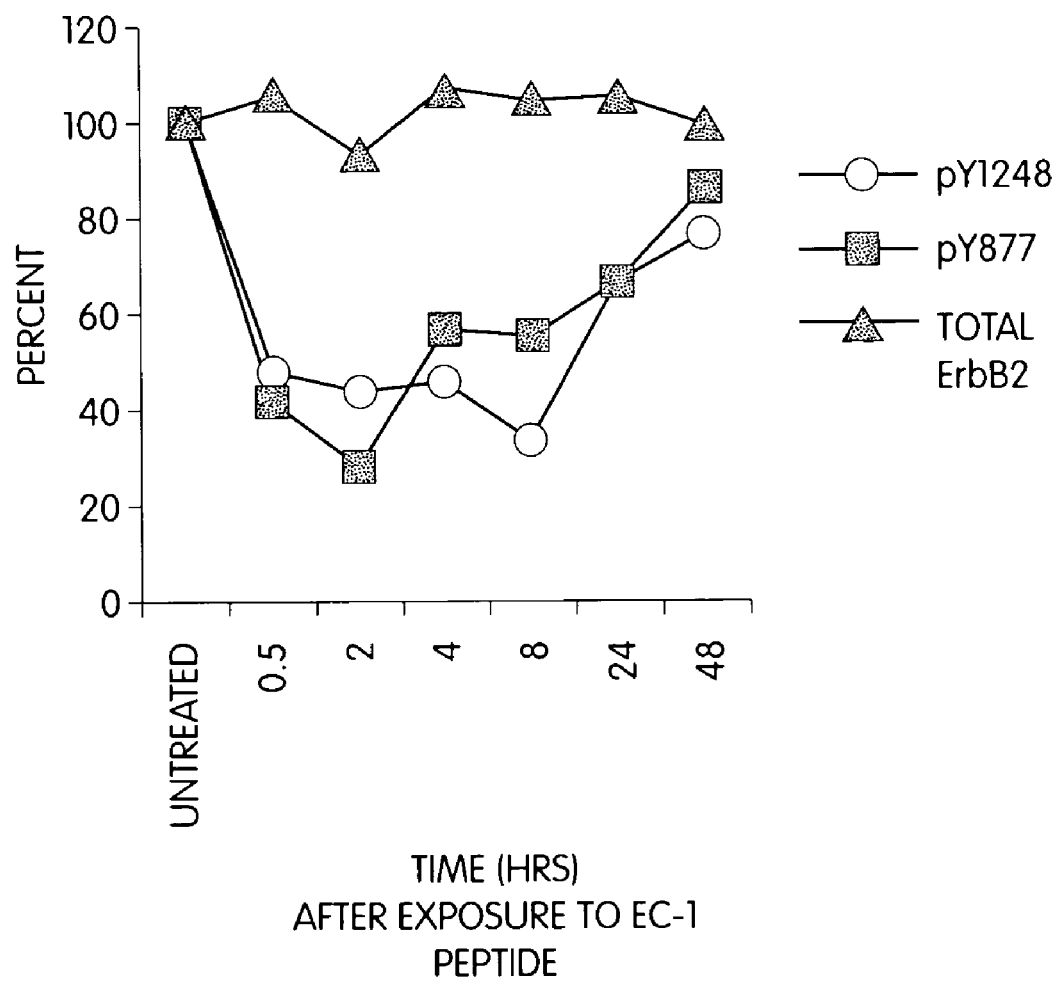
FIG. 6B is a graph showing the densitometric analysis of the Western blots shown in FIG. 6A. The graph shows that EC-1 peptide exposure inhibits phosphorylation of ErbB2 on tyrosine residues pY877 and pY1248 but has no effect on the total expression level of ErbB2.

ErbB2 overexpressing SKBR3 cells were treated with the EC-1 free peptide to determine its effect on ErbB2 activation. When ErbB2 is activated it becomes phosphorylated on specific tyrosine residues (i.e., pY1248 and pY877). This is turn triggers downstream signal transduction events, culminating in increased cellular proliferation. Viable SKBR3 cells were treated with 25 μM EC-1 peptide for 15 minutes. At 0.5, 2, 4, 8, 22 and 48 hours thereafter, cell lysates were prepared and run on a Western blot using phospho-specific ErbB2 antibodies. (See FIG. 6A.) Densitometric analysis of the Western blots showed that EC-1 peptide inhibits 40% of the phosphorylation of residues pY1248 and pY877 after 0.5 hrs. The results demonstrate that 25 μM EC-1 inhibits the phosphorylation of ErbB2 for at least 8 hours after treatment. (See FIG. 6B.) The peptide had no effect on total ErbB2 expression.

Example 4

Localization of Agents to and Within ErbB2 Expressing Cells

EBP either unconjugated or conjugated to a therapeutic agent such as a cytotoxic agent are produced. These peptides are tested in the following assays with the SKBR3 and BT474 cell lines that are known to overexpress ErbB2, cell lines that express low levels of ErbB2 (MCF-7) and breast cells that do not overexpress ErbB2 (Hs 578Bst) as controls. These cell lines are tested using the following assays: a)

viability by trypan blue and hemocytometer counts (standard); b) cell proliferation by MTT assay (Hansen et al. J. Immunol. Meth. 119:203–210, 1989); c) cell proliferation by BrdU assay (Roche); d) clonogenic assays (as described above); e) human breast cancer xenografts in nude mice (as described above).

The peptides are modified, depending on the results of the above assays, using mutagenesis phage display technology and medicinal chemistry techniques. For example, peptides that require a cyclic structure may have their disulfide bond changed to a thioether bond, to increase stability in vivo (Oligino et al., JBC 272:29046).

The cytotoxicity and specificity of the therapeutic for ErbB2 expressing cells, in vitro, in animal models, and in clinical studies, can be significantly improved by covalent attachment to an EBP. EBP in an unconjugated form can effectively inhibit the function of ErbB2 (including the susceptibility of ErbB2 to phosphorylation) and, therefore, the proliferation of cells overexpressing ErbB2. Inhibition of proliferation can ameliorate disease caused by the overexpression of ErbB2 directly and/or can lead to induction of apoptosis of cells overexpressing ErbB2.

The EBP can also be used in some embodiments to modulate trafficking of agents within a cell. Some EBP are capable of localizing therapeutic agents preferentially in the cytoplasm, while others allow movement into the nucleus. Agents that exert their effects in the cytoplasm can be conjugated to the EBP described herein in order to increase their concentration in the cytoplasm.

Equivalents

It should be understood that the preceding is merely a detailed description of certain preferred embodiments. It therefore should be apparent to those of ordinary skill in the art that various modifications and equivalents can be made without departing from the spirit and scope of the invention. It is intended that the invention encompass all such modifications within the scope of the appended claims.

All references, patents and patent applications and publications that are cited or referred to in this application are incorporated in their entirety herein by reference.

We claim:

1. A composition comprising a peptide comprising an ErbB2 binding peptide (EBP) that binds specifically to the extracellular domain of ErbB2, wherein the ErbB2 binding peptide is between 11 and 20 amino acids in length; comprises at least two cysteines separated by 9 or 10 amino acids; and the amino acid sequence of residues 1–4 at the N-terminal end of the ErbB2 binding peptide is WTGW (SEQ ID NO:47).

2. The composition of claim 1, wherein the peptide is cyclic.

3. The composition of claim 1, wherein the peptide is conjugated to an agent.

4. The composition of claim 3, wherein the agent is selected from the group consisting of a toxin, a radioactive molecule, a detectable label, an imaging agent, a chemotherapeutic agent, a diagnostic agent, an anti-cancer agent, an anti-angiogenic agent, an apoptosis agent, a translocating agent, and an immunomodulatory agent.

5. The composition of claim 1, wherein the peptide is selected from the group consisting of a phage display peptide library member, a synthetic peptide library member, a combinatorial chemistry library member and a peptidomimetic.

6. The composition of claim 1, further comprising a pharmaceutically acceptable carrier.

7. The composition of claim 1, further comprising an anti-cancer agent.

8. The composition of claim 1, wherein the composition is in a sustained release vehicle.

9. The composition of claim 1, wherein the ErbB2 binding peptide inhibits phosphorylation of ErbB2.

* * * * *